(12) United States Patent
Swisher

(10) Patent No.: US 10,434,036 B2
(45) Date of Patent: Oct. 8, 2019

(54) HIGH-FLOW ENTERAL FEEDING SYRINGE ASSEMBLY

(71) Applicant: KPR U.S., LLC

(72) Inventor: David Rork Swisher, St. Charles, MO (US)

(73) Assignee: KPR U.S., LLC, Mansfield, MA (US)

( * ) Notice: Subject to any disclaimer, the term of this patent is extended or adjusted under 35 U.S.C. 154(b) by 212 days.

(21) Appl. No.: 15/367,687

(22) Filed: Dec. 2, 2016

(65) Prior Publication Data

US 2017/0156988 A1 Jun. 8, 2017

Related U.S. Application Data

(60) Provisional application No. 62/263,585, filed on Dec. 4, 2015, provisional application No. 62/264,070, filed on Dec. 7, 2015.

(51) Int. Cl.
  *A61M 39/10* (2006.01)
  *A61J 15/00* (2006.01)
  *A61M 39/26* (2006.01)

(52) U.S. Cl.
  CPC ....... *A61J 15/0076* (2015.05); *A61J 15/0015* (2013.01); *A61J 15/0026* (2013.01); *A61M 39/10* (2013.01); *A61M 39/26* (2013.01); *A61M 2039/1033* (2013.01); *A61M 2039/1038* (2013.01); *A61M 2039/1088* (2013.01); *A61M 2039/1094* (2013.01); *A61M 2206/20* (2013.01)

(58) Field of Classification Search
  CPC ................ A61J 15/0015; A61J 15/0026; A61J 15/0076; A61M 2039/1033; A61M 2039/1038; A61M 2039/1088; A61M 2039/1094; A61M 2206/20; A61M 39/10; A61M 39/26

See application file for complete search history.

(56) References Cited

U.S. PATENT DOCUMENTS

| | | | |
|---|---|---|---|
| 8,777,930 | B2 | 7/2014 | Swisher et al. |
| 2005/0090805 | A1 | 4/2005 | Shaw et al. |
| 2008/0183153 | A1 | 7/2008 | Frederick |
| 2010/0331787 | A1 | 12/2010 | Fournie |

FOREIGN PATENT DOCUMENTS

| | | |
|---|---|---|
| EP | 0093837 A1 | 11/1983 |
| WO | 2004082756 A1 | 9/2004 |

OTHER PUBLICATIONS

"Alternate Syringes: Low Displacement Option," Rork Swisher, ISO 80369 Series Meeting, Berlin, Germany, Mar. 19, 2014, 11 pages.
International Search Report dated Apr. 21, 2017 in related International Application No. PCT/US2016/064715, 7 pages.
Written Opinion of the International Searching Authority dated Apr. 21, 2017 in related International Application No. PCT/US2016/064715, 9 pages.

*Primary Examiner* — Imani N Hayman

(57) ABSTRACT

An enteral feeding connector facilitates an increased flow rate into and through the connector to accommodate feeding fluids requiring higher flow rates for delivery. The connector includes a male connector portion including an inlet, a fluid passage in fluid communication with the inlet, and at least one connector projection at the inlet. The connector projection defines a cross-sectional area of the inlet configured to facilitate delivering feeding fluid requiring higher flow rates through the connector.

12 Claims, 27 Drawing Sheets

HIGH-FLOW ENTERAL FEEDING SYRINGE ASSEMBLY

CROSS-REFERENCE TO RELATED APPLICATION

This application claims the benefit of priority under 35 U.S.C. § 119 to U.S. Patent Application No. 62/263,585, titled HIGH-FLOW ENTERAL FEEDING SYRINGE ASSEMBLY, which was filed on Dec. 4, 2015, and U.S. Patent Application No. 62/264,070, titled HIGH-FLOW ENTERAL FEEDING SYRINGE ASSEMBLY, which was filed on Dec. 7, 2015, and which are incorporated herein by reference in their entireties for all purposes.

BACKGROUND

The present disclosure generally relates to a high-flow enteral feeding syringe assembly. In a medical environment, many devices have tubing or other fluid conduits adapted for manual connection in order to provide a fluid connection between devices or between a device and a patient including enteral feeding pumps and enteral feeding lines. For example, enteral feeding or delivery of medicines to the gastrointestinal tract may be accomplished by connecting an enteral feeding connector to an oral syringe. Some patients, such as home healthcare patients, desire nutritional fluid that is relatively thick. For instance, patients may desire the delivery of blended fruits, vegetables, and other foods via enteral feeding.

FIG. 1 shows a conventional enteral feeding connector assembly including a male enteral feeding connector 1 and a female enteral feeding connector 3, included as part of a syringe barrel, configured to be connected to one another for use in connecting the syringe barrel to medical tubing 5. The female enteral feeding connector 3 receives a male connector portion 7 of the male enteral feeding connector 1 within an interior space 9 of the female connector. An exterior surface of the male connector portion 7 engages and seals with an interior surface of the female enteral feeding connector 3 to achieve a fluid-tight connection placing an interior of the syringe barrel in fluid communication with a passage in the medical tubing 5. Fluid is typically delivered from the female connector 3 to the male connector 1. A barrel outlet 11 is located adjacent an inlet 13 of the male enteral feeding connector 1 and communicates with a flow passage 15 in the male connector. The barrel outlet 11 and connector inlet 13 are sized and arranged to comply with ISO standards 80369-3 (proposed) and 80369-20 to prevent misconnection of the connectors 3, 1 with unauthorized connectors. An example of an unauthorized connector is an IV tube or IV connector. However, to achieve this purpose, the barrel outlet 11 has a reduced diameter section 17 that can choke fluid flow exiting the syringe barrel. Additionally, the inlet 13 and diameter of the flow passage 15 in the male connector 1 may also choke fluid flow into and through the enteral feeding connector assembly.

SUMMARY

The present disclosure is directed to a high-flow enteral feeding syringe assembly complying with ISO standards to prevent misconnection with unauthorized connectors.

In one aspect, a An enteral feeding syringe assembly comprises a syringe including a barrel and a connector portion having a syringe fluid passage in fluid communication with the barrel and extending through the connector portion to an port of the syringe. The syringe fluid passage includes a main portion defining a centerline of the syringe fluid passage and a constricted portion. The constricted portion includes a first axially facing blocking surface of the connector portion defining at least a portion of a boundary of the constricted portion of the syringe fluid passage, a second axially facing surface located on a diametrically opposite side of the centerline from the first axially facing surface and defining at least a portion of the boundary of the constricted portion, and a third axially facing surface angularly offset about the centerline from the first axially facing surface and defining at least a portion of the boundary of the constricted portion. The third axially facing surface is spaced from the centerline a distance greater than at least one of the first and second axially facing surfaces. A connector configured for attachment to the syringe to connect the syringe in fluid communication with a fluid containment device comprises a male connector portion receivable in the fluid passage of the syringe connector portion. The male connector has a connector fluid passage extending through the connector. The connector fluid passage includes a main portion defining a centerline of the connector fluid passage and a constricted portion. The constricted portion including a first axially facing blocking surface of the connector portion defining at least a portion of a boundary of the constricted portion of the connector fluid passage, a second axially facing surface located on a diametrically opposite side of the centerline from the first axially facing surface and defining at least a portion of the boundary of the constricted portion, and a third axially facing surface angularly offset about the centerline from the first axially facing surface and defining at least a portion of the boundary of the constricted portion. The third axially facing surface being spaced from the centerline a distance greater than at least one of the first and second axially facing surfaces.

In some embodiments, the connector portion of the syringe further comprises a connector projection of the connector portion extending toward the centerline of the syringe fluid passage, the first axial surface being defined on the connector projection.

In certain embodiments, the connector projection of the syringe extends laterally across the syringe fluid passage of the connector portion of the syringe.

In some embodiments, the connector projection of the syringe comprises a first connector projection of the syringe. The syringe further comprises a second connector projection disposed on an opposite side of the centerline. The second connector projection extends laterally across the syringe fluid passage of the connector portion of the syringe, and the second axially facing surface is defined on the second connector projection.

In certain embodiments, the distance between the first and second axially facing surfaces is about 2.90 mm (0.11 in.) or less.

In some embodiments, the male connector portion of the connector comprises a connector projection extending toward the centerline of the connector fluid passage. The first axial surface of the male connector portion is defined in the connector projection.

In certain embodiments, the connector projection of the male connector portion of the connector extends laterally across the fluid passage of the connector. The connector projection of the male connector portion is configured to extend into the syringe fluid passage of the connector portion of the syringe and make a sealing connection with the connector portion of the syringe when the connector is attached to the syringe.

In some embodiments, the connector projection of the connector comprises a first connector projection of the connector. The connector comprises a second connector projection disposed on an opposite side of the fluid passage of the connector. The second connector projection of the connector extends laterally across the fluid passage of the connector, and the second axially facing surface is defined on the second connector projection.

In certain embodiments, the distance between the first and second axially facing surfaces of the male connector portion of the connector is about 2.90 mm (0.11 in.) or less.

In some embodiments, the connector projection of the connector extends laterally across the fluid passage of the connector from one side of the fluid passage to the diametrically opposite side of the fluid passage.

In certain embodiments, the connector projection of the connector includes a first portion extending away from the male connector portion at an angle toward a central longitudinal axis of the male connector portion, and a second portion extending from the first portion generally perpendicular to the central longitudinal axis of the male connector portion.

In some embodiments, the male connector portion includes at least one cutout in the male connector portion. The cutout provides an augmented area portion enhancing fluid flow in the passage of the male connector portion.

In another aspect, an enteral feeding syringe facilitating an increased flow rate out of the syringe to accommodate feeding fluids requiring higher flow rates for delivery generally comprises a body having an interior chamber and an outlet. A female connector portion attached to the body includes a syringe fluid passage in fluid communication with the interior chamber and a pair of connector projections at the outlet. The connector projections extend laterally across the outlet into the syringe fluid passage of the female connector portion and define a cross-sectional area of the outlet configured to facilitate delivering feeding fluid requiring higher flow rates through the syringe.

In certain embodiments, the connector projections define an outlet diameter in conformity with ISO standards 80369-3 and 80369-20 to prevent misconnection of the syringe with an unauthorized connector.

In some embodiments, the outlet diameter is not larger than about 2.90 mm (0.11 in.).

In certain embodiments, the outlet has a cross-sectional area of about 18.35 mm$^2$ (0.03 in.$^2$) enhancing fluid flow out of the outlet to facilitate delivering feeding fluid requiring higher flow rates through the syringe.

In yet another aspect, an enteral feeding connector facilitating an increased flow rate into and through the connector to accommodate feeding fluids requiring higher flow rates for delivery generally comprises a male connector portion including an inlet, a fluid passage is in fluid communication with the inlet, and at least one connector projection at the inlet. The connector projection defines a cross-sectional area of the inlet configured to facilitate delivering feeding fluid requiring higher flow rates through the connector. A tube connector portion is attached to the male connector portion.

In some embodiments, the at least one connector projection defines an inlet diameter in conformity with ISO standards 80369-3 and 80369-20 to prevent misconnection of the connector with an unauthorized connector.

In certain embodiments, the inlet diameter is not larger than about 2.90 mm (0.11 in.).

In some embodiments, the inlet has a cross-sectional area of about 12.09 mm$^2$ (0.02 in.$^2$) enhancing fluid flow into the inlet to facilitate delivering feeding fluid requiring higher flow rates through the connector.

In certain embodiments, the enteral feeding connector further comprises a pair of connector projections disposed on opposite sides of the inlet.

Embodiments can include one or more of the following advantages.

In some embodiments, an increased flow rate of feeding fluid through the assembly is achieved.

In other embodiments, relatively thick nutritional fluid can be delivered through the assembly without significant backup in the assembly.

In some embodiments, misconnection with unauthorized connectors is prevented.

Other aspects, features, and advantages will be apparent from the description and drawings, and from the claims.

BRIEF DESCRIPTION OF THE DRAWINGS

Corresponding reference characters indicate corresponding parts throughout the drawings.

DETAILED DESCRIPTION OF THE DRAWINGS

Figure 2:
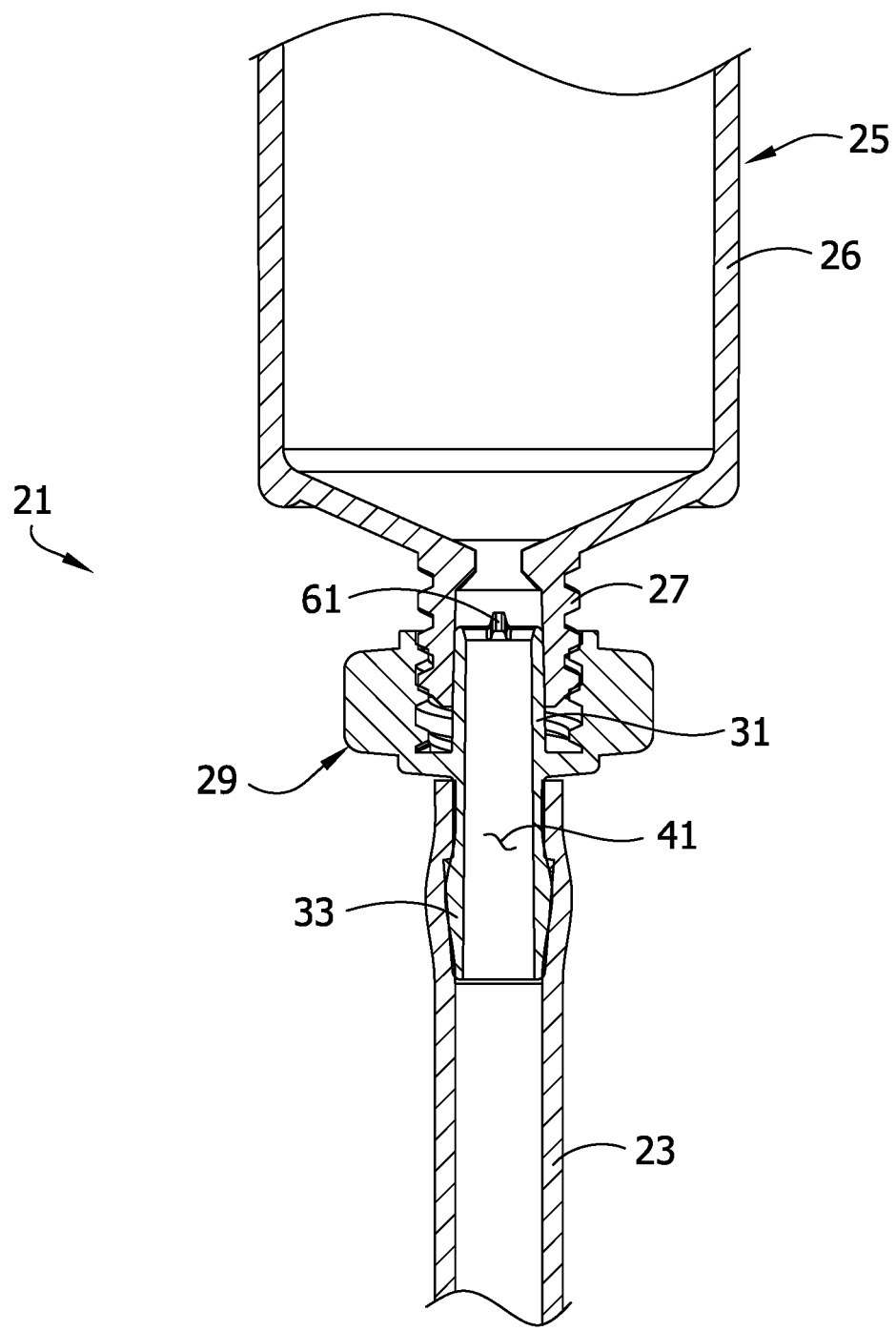
FIG. 2 is a fragmentary longitudinal section of an enteral feeding syringe assembly constructed according to the principles of the present invention.
Figure 3:
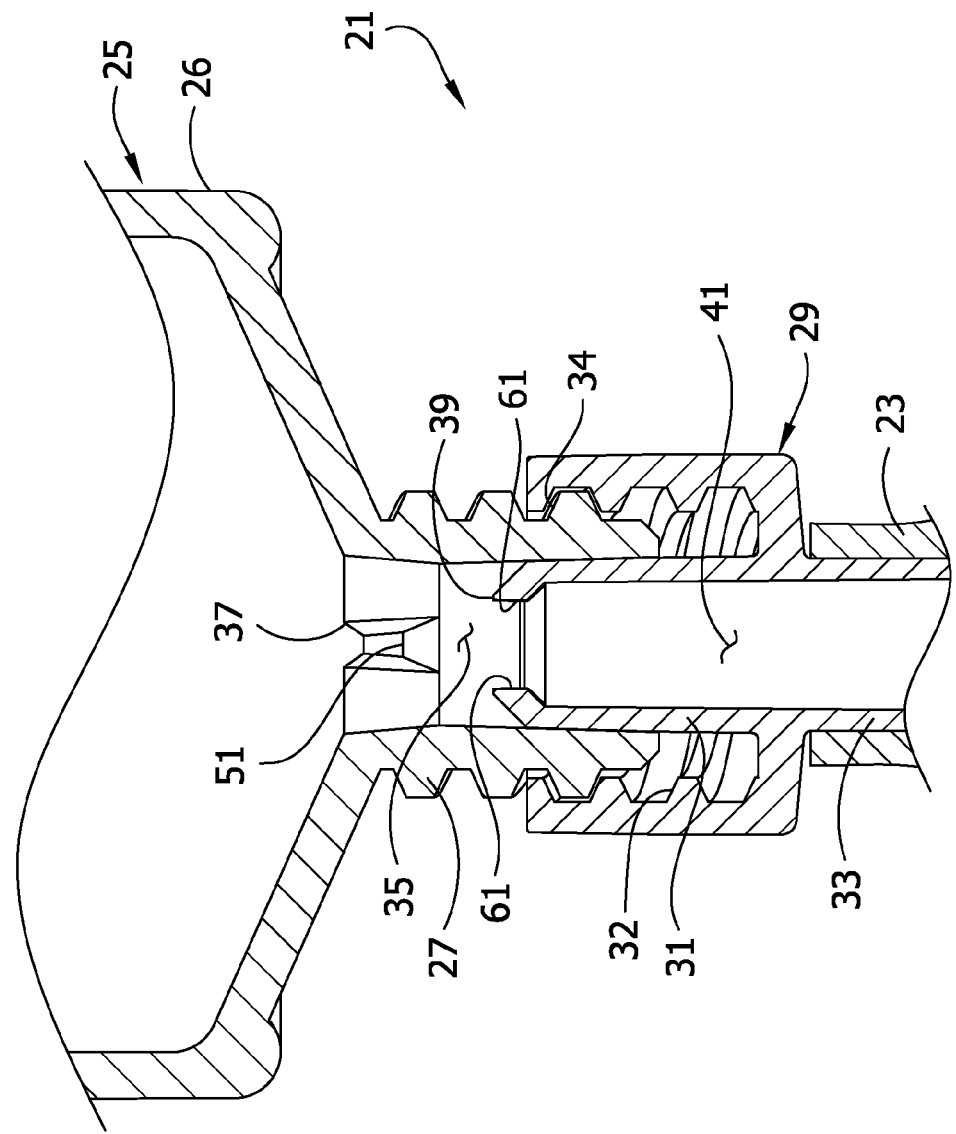
FIG. 3 is a an enlarged fragmentary longitudinal section of the enteral feeding assembly of FIG. 2 taken in a plane perpendicular to section shown in FIG. 2.

Referring to FIGS. 2 and 3, an enteral feeding syringe assembly is generally indicated at 21. The syringe assembly is configured to fluidly connect to a fluid conduit (e.g., feeding tube 23) or a reservoir (e.g., medical tubing, bottle, nutrient bag, etc.) for retrieving fluid from the fluid reservoir or delivering fluid to a subject through the fluid conduit. The syringe assembly 21 comprises a syringe 25 including a barrel 26 and a female connector 27 on a distal end of the syringe. The assembly 21 further comprises a male enteral feeding connector 29 including a male connector portion 31 for providing a sealed connection with the female connector 27 on the syringe 25 when the enteral feeding connector is secured (e.g., threaded via threads 32 and 34 on the male connector 29 and female connector 27, respectively) onto the female connector of the syringe. When the enteral feeding connector 29 is properly secured to the syringe 25, a tube connector portion 33 of the enteral feeding connector can be connected to a fluid conduit (e.g., feeding tube 23) or reservoir to fluidly connect the syringe to the fluid conduit or reservoir. A fluid conduit and a reservoir may each be broadly considered a "fluid containment device" for purposes of the present description. A plunger (not shown) can be used to discharge fluid from the syringe 25 and to draw fluid into the syringe. In the illustrated embodiment, the female connector 27 is formed as one piece of material with a remainder of the syringe 25 including the barrel 26. However, the female connector 27 could be formed separately from the syringe 25 and suitably attached to the syringe.

Figure 4:
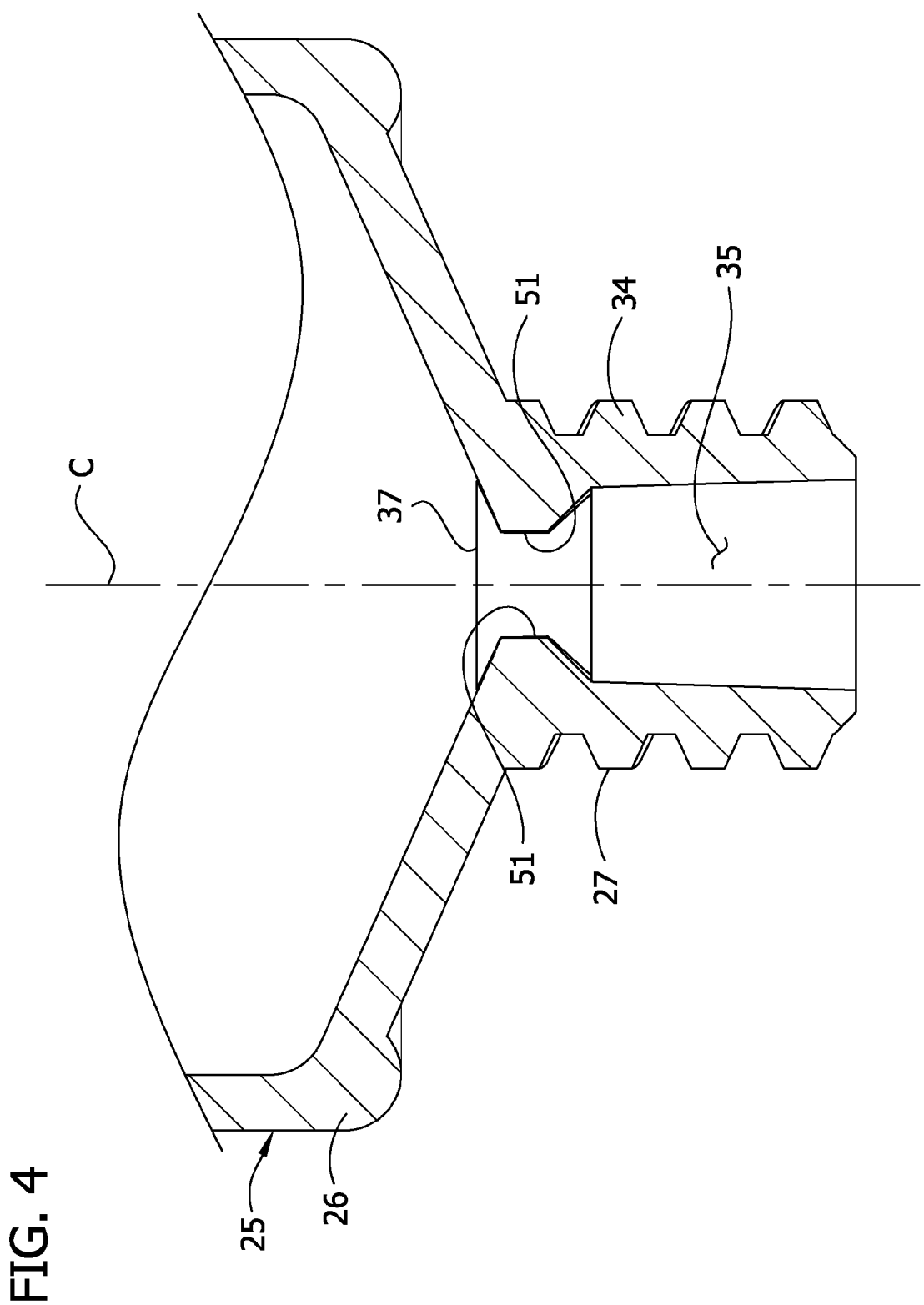
FIG. 4 is an enlarged fragmentary longitudinal section of a syringe of the enteral feeding syringe assembly of FIG. 2.
Figure 5:
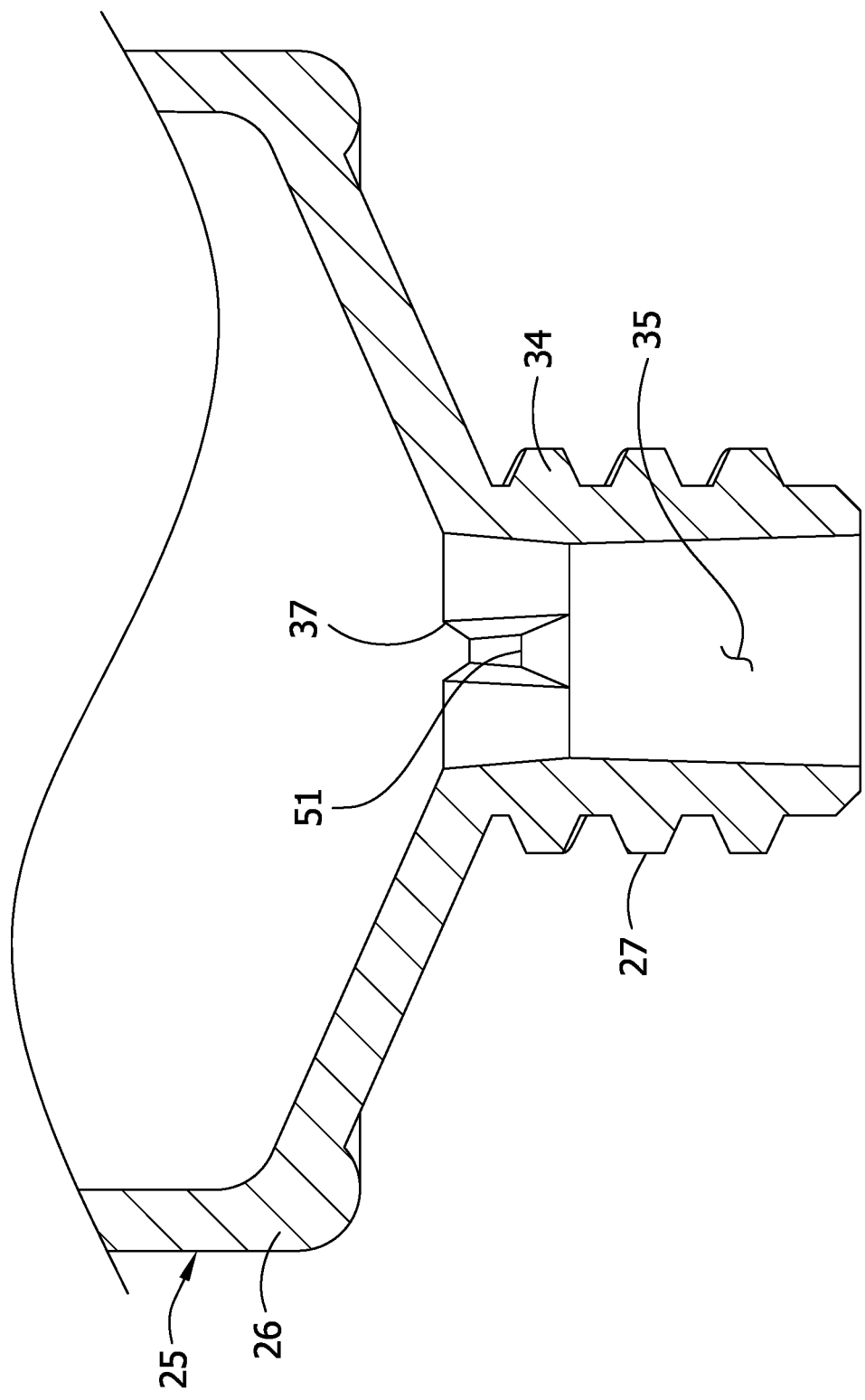
FIG. 5 is an enlarged fragmentary longitudinal section of the syringe taken in a plane perpendicular to the section shown in FIG. 4.

Referring to FIGS. 3-5, the enteral feeding syringe assembly 21 is configured to permit relatively thick nutritional fluid, which may even include bits of solid food, to be delivered through the assembly while protecting against improper connections. In particular, the enteral feeding syringe assembly 21 allows for fluid to pass through the assembly at an increased flow rate, even under gravity feed. The enteral feeding syringe assembly also reduces the opportunity for occlusion. The female connector 27 receives the male connector portion 31 of the male enteral feeding connector 29 within an interior space 35 of the female connector. An exterior surface of the male connector portion 31 engages and seals with an interior surface of the female enteral feeding connector 27 to achieve a fluid-tight connection placing an interior of the syringe 25 in fluid communication with a passage in the feeding tube 23. A barrel outlet 37 is located adjacent an inlet 39 of the enteral feeding connector 29 and communicates with a flow passage 41 in the male connector portion 31. The barrel outlet 37 has an augmented area section 43 (FIG. 7) that enhances fluid flow exiting the syringe barrel as compared to the barrel outlet 11 (FIG. 1) of the female connector 3 of the prior art. The inlet 39 of the enteral feeding connector 29 also has an augmented area section 45 (FIG. 12) as compared to the inlet 13 (FIG. 1) of the male connector 1 of the prior art that enhances fluid flow into the enteral feeding connector. Additionally, flow passage 41 has a larger cross-sectional area than the flow passage 15 of the male connector 1 of the prior art which enhances fluid flow through the enteral feeding connector. Enhancing the fluid flow through the enteral feeding connector assembly 21 facilitates delivering relatively thick nutritional fluid through the assembly.

Figure 6:
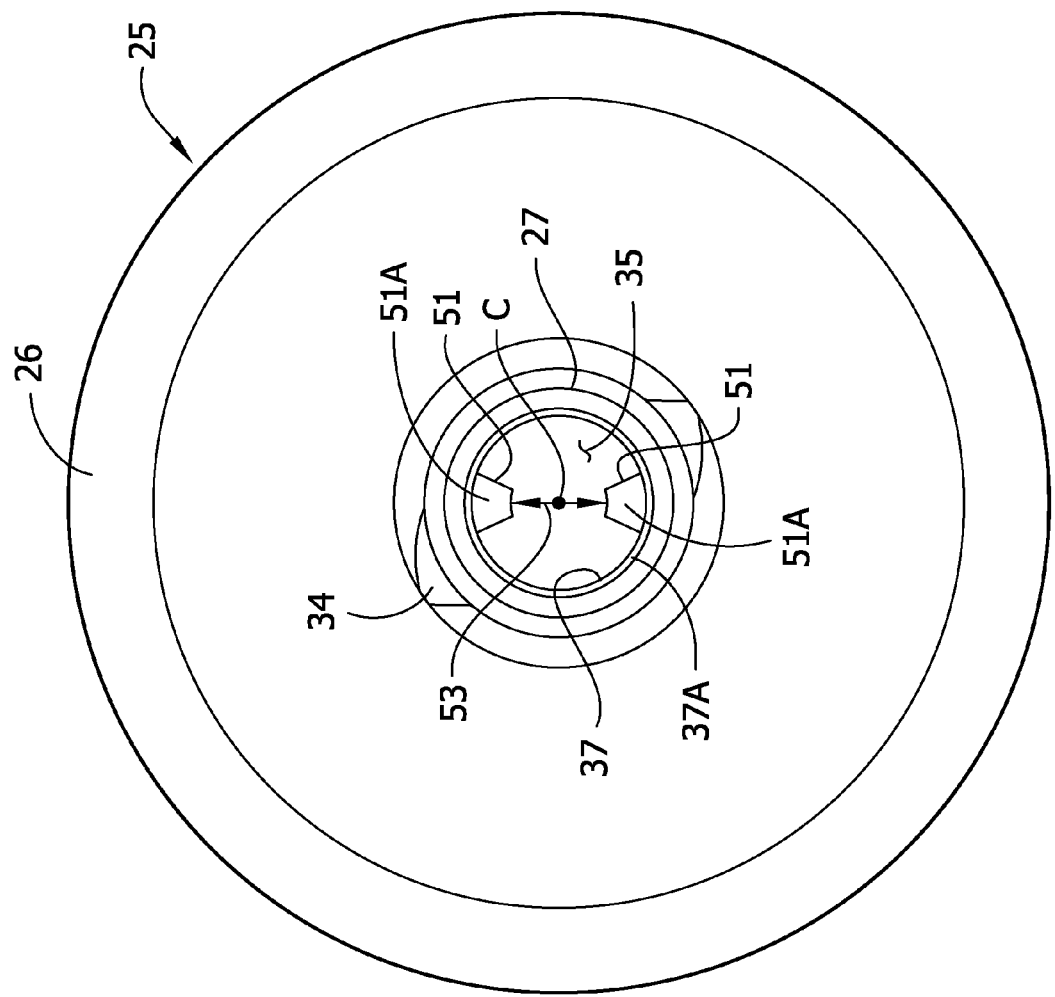
FIG. 6 is an end view of the syringe.
Figure 7:
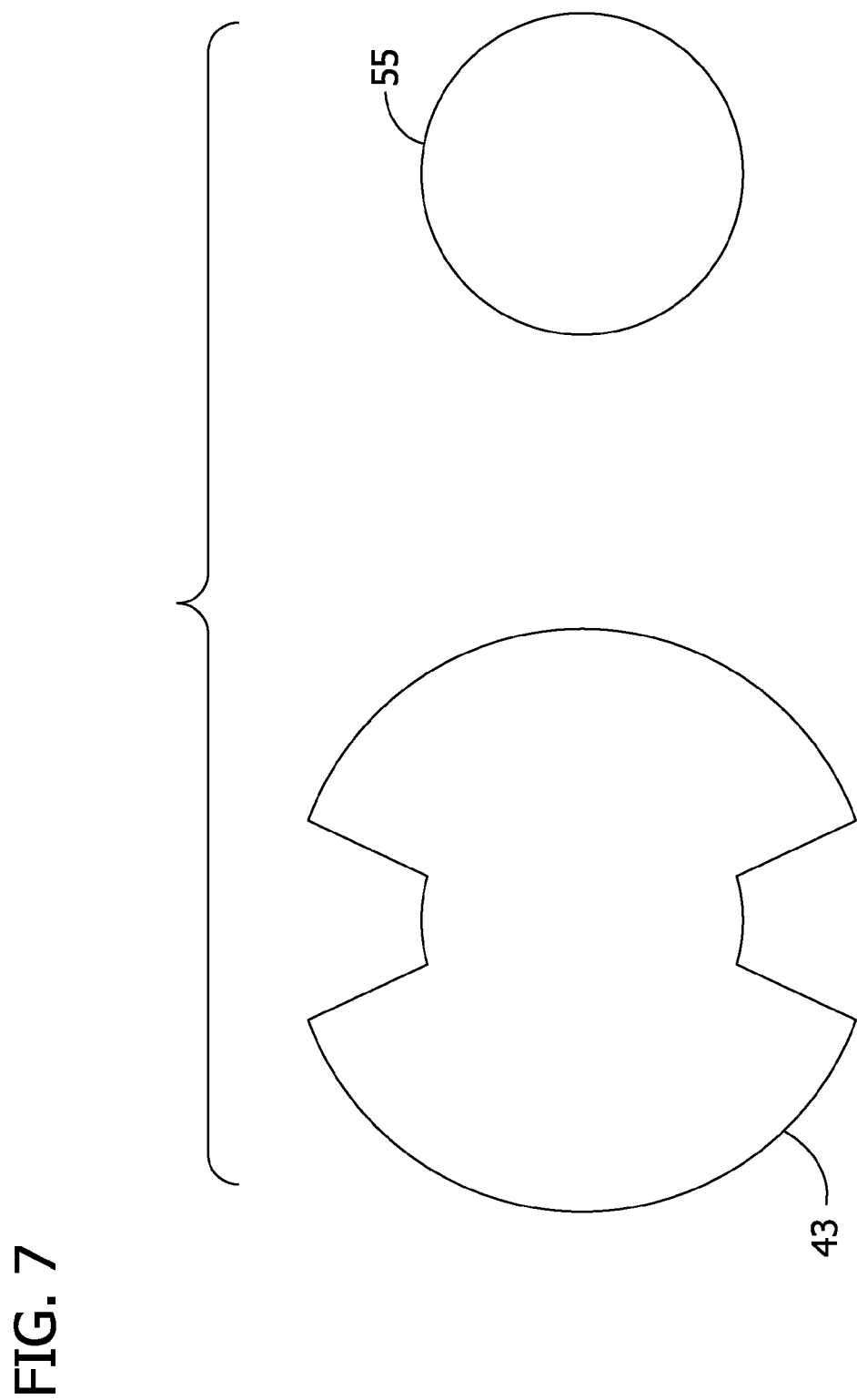
FIG. 7 is a schematic illustration comparing an opening of the syringe to a syringe opening of the prior art.
Figure 8:
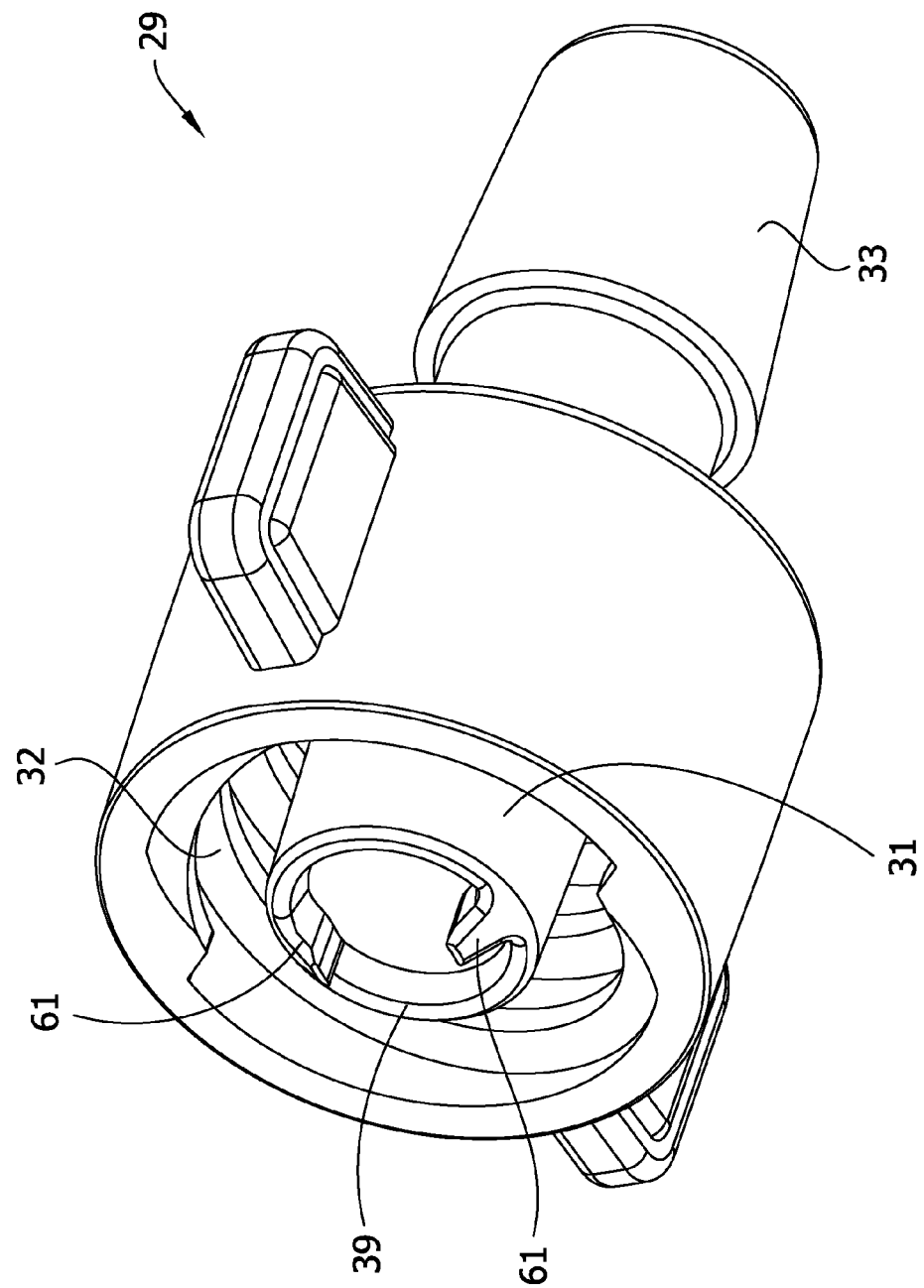
FIG. 8 is a perspective of a connector of the enteral feeding syringe assembly of FIG. 2.
Figure 9:
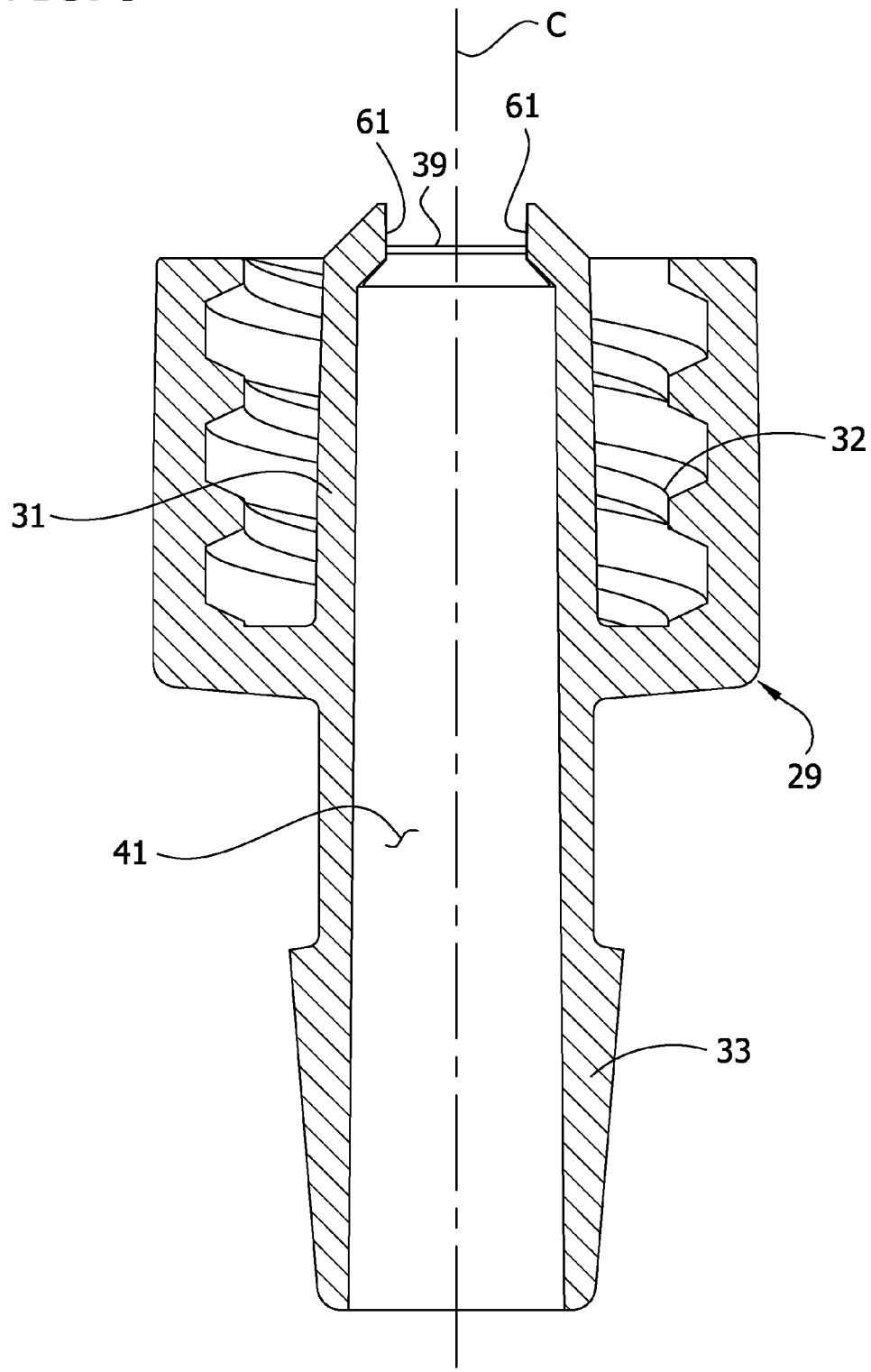
FIG. 9 is longitudinal section of the connector of FIG. 8.
Figure 10:
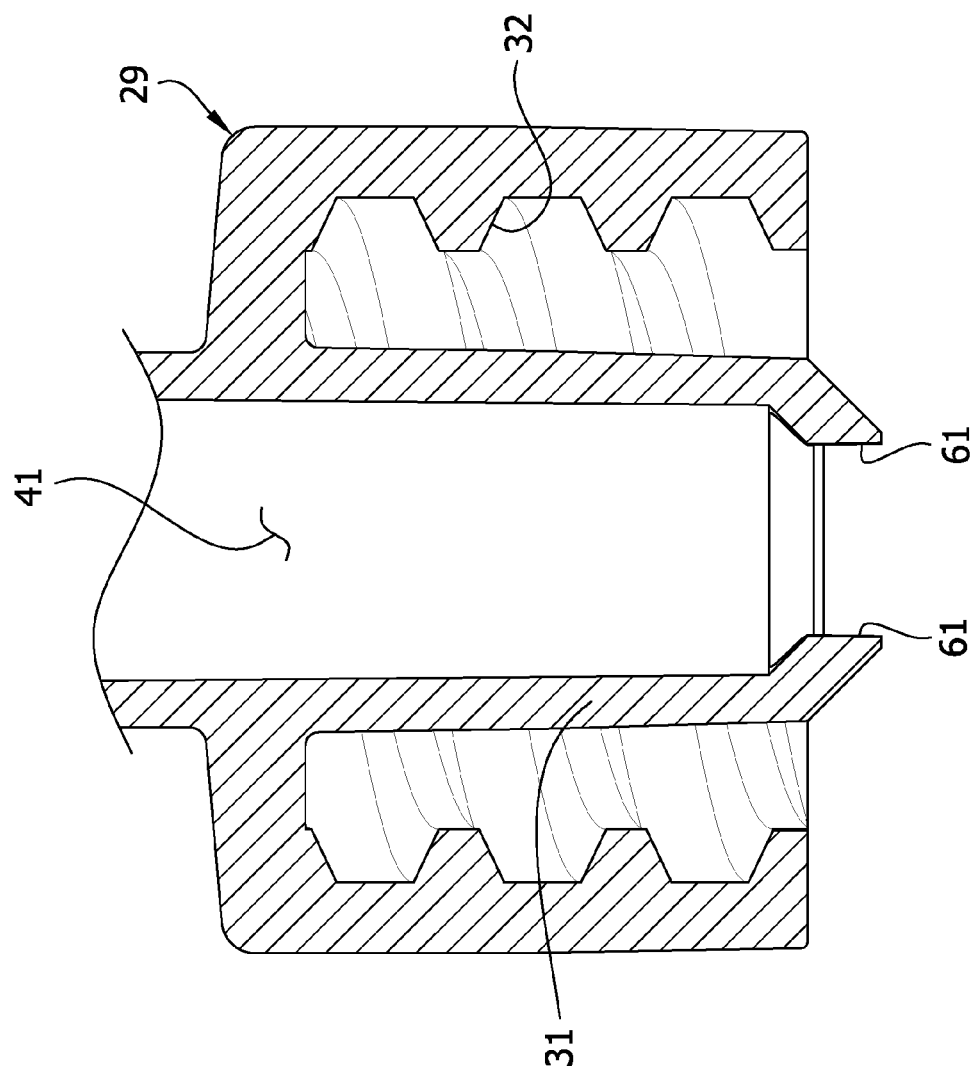
FIG. 10 is an enlarged fragmentary longitudinal section of the connector of FIG. 8.
Figure 11:
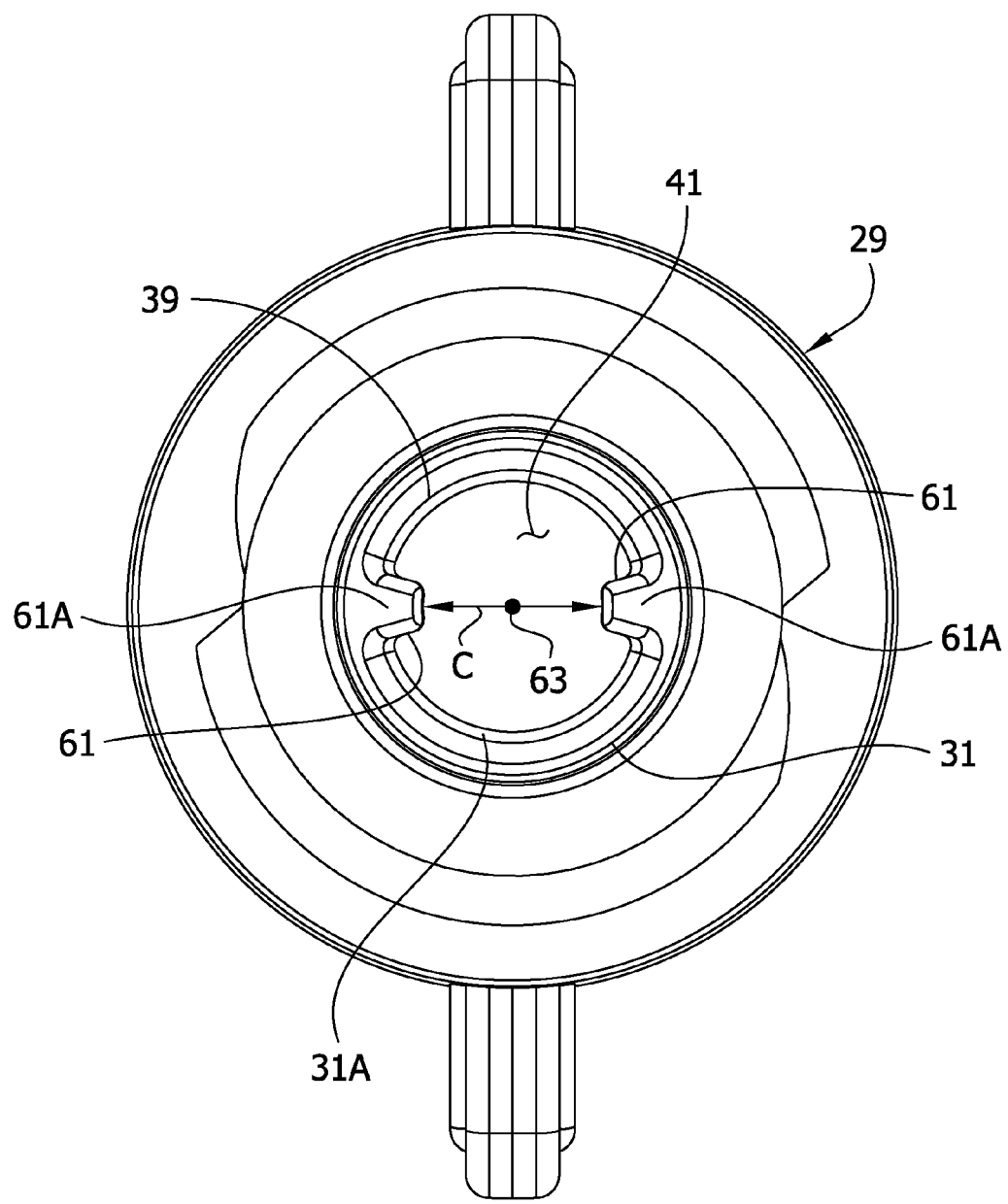
FIG. 11 is an end view of the connector.

Referring to FIGS. 6 and 7, (first and second) connector projections 51 extend from the barrel outlet 37 into the interior space 35 of the female connector 27. The connector projections 51 provide an opening diameter 53 (FIG. 6) that conforms to ISO standards 80369-3 (proposed) and 80369-20 to prevent misconnection of the female connector 27 with an unauthorized connector. In one embodiment, the opening diameter 53 is not larger than about 2.90 mm (0.11 in.). It will be appreciated that the projections 51 somewhat constrict the cross-sectional area of the interior space 35 (see, FIG. 4). Referring particularly to FIG. 6, the opening of the interior space 35 at the location of the projections 51 is considered to be the constricted portion of the interior space. Each of the connector projections 51 defines an axially facing surface 51A. A third axially facing surface is defined at 37A by the end of the barrel outlet 37. The radially inner edges of these (first and second) axially facing surfaces 51A define opposite edges of part of the boundary of the constricted portion of the interior space 35. The radially inner edge of the axially facing surface 37A defines another part of the boundary of the constricted portion. It may be seen in FIG. 6, that the axially facing surface 37A is spaced from a centerline C (seen end on, as a point in FIG. 6) a distance greater than both of the axially facing surfaces 51A. The axially facing surface 37A is also offset along the centerline C from the axially facing surfaces 51A. As a result of this configuration of the constricted portion, the overall cross-sectional area of the interior space 35 at the constricted portion remains relatively large as schematically illustrated by section 43 in FIG. 7. Section 43 is juxtaposed in FIG. 7 with a section 55 showing the area of the barrel outlet 11 of the prior art. As can be seen in FIG. 7, the cross-sectional area of the barrel outlet 37 (section 43) is significantly larger than the cross-sectional area of the barrel outlet 11 (section 55). In one embodiment, the cross-sectional area of the augmented area section 43 is about 18.4 mm$^2$ (0.03 in.$^2$) and the cross-sectional area of section 55 is about 6.6 mm$^2$ (0.01 in.$^2$). In one embodiment, the cross-sectional area of the augmented area section 43 is over 270% larger than the cross-sectional area of section 55. Thus, the increased cross-sectional area for the barrel outlet 37 of the assembly 21 allows for passage of liquid that is thick and may include bits of solid, such as from ground fruit. The greater area also permits a greater flow rate to be generated at the barrel outlet than can be generated with the cross-sectional area of the barrel outlet 11 of the prior art. In the illustrated embodiment, there are two connector projections 51 disposed on opposite sides of the female connector 27. It is envisioned, however, that any number of connector projections can be utilized. Additionally, other components for producing the opening diameter 53 in conformity of ISO standards 80369-3 (proposed) and 80369-20 are envisioned. For instance, cross ribs, bridges, and other projections disposed at different angles could be used to accomplish the increased flow rate and reduced potential for occlusion while still conforming to the ISO standards.

Figure 1:
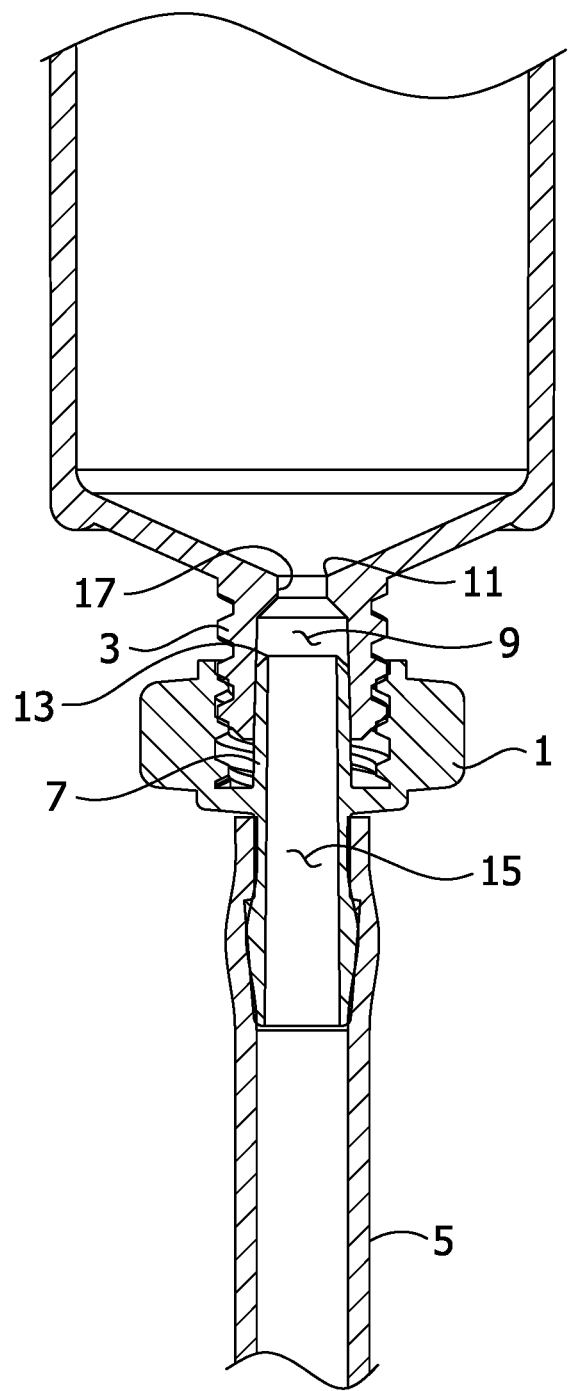
FIG. 1 is a fragmentary longitudinal section of a prior art enteral feeding syringe assembly.
Figure 12:
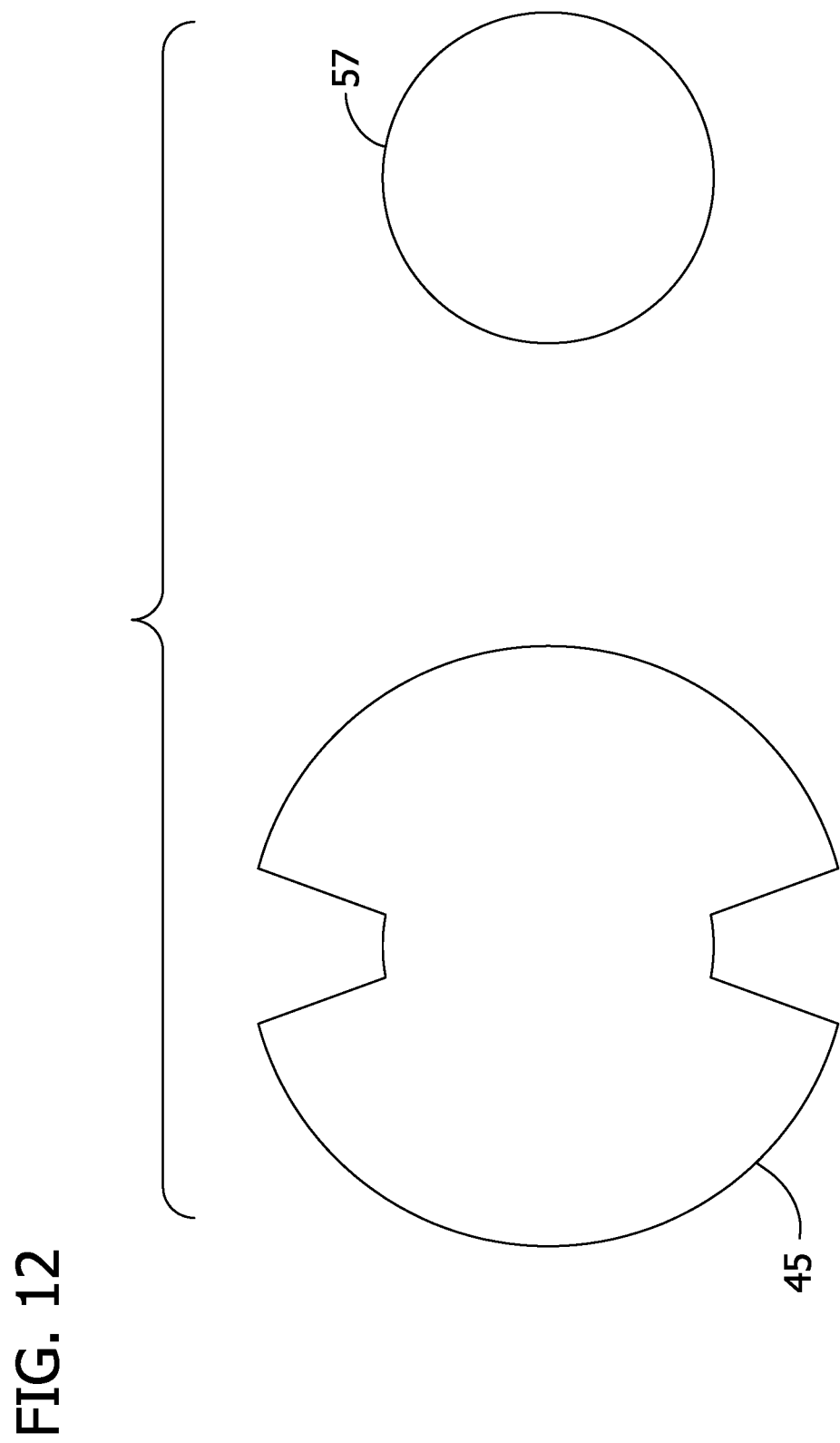
FIG. 12 is a schematic illustration comparing an opening of the connector to a connector opening of the prior art.

Referring to FIGS. 8-12, (first and second) connector projections 61 at the inlet 39 of the enteral feeding connector 29 extend from the male connector portion 31. When the enteral feeding connector 29 is connected to the female connector 27, the connector projections 61 extend into the interior space 35 of the female connector. The connector projections 61 provide an opening diameter 63 (FIG. 11) that conforms to ISO standards 80369-3 (proposed) and 80369-20 to prevent misconnection of the enteral feeding connector 29 with an unauthorized connector. In one embodiment, the opening diameter 63 is not larger than about 2.90 mm (0.11 in.). The diameter 63 also represents a constricted portion of the flow passage 41. Each of the connector projections 61 defines an axially facing surface 61A. The projections 61 somewhat constrict the cross-sectional area of the flow passage 41 (see, FIG. 9). The radially inner edges of the (first and second) axially facing surfaces 61A define the boundary of the constricted portion 63 of the flow passage 41. However, the overall constriction of the flow passage 41 is limited by the configuration of the male connector 29. A third axially facing surface 31a is defined at the end of the male connector portion 31. The radially inner edge of the axially facing surface 31A also defines a portion of the cross sectional area of the flow passage 41. It may be seen in FIG. 11, that the axially facing surface 31A is spaced from a centerline C (seen end on, as a point in FIG. 11) a distance greater than both of the axially facing surfaces 61A. The cross section of the flow passage 41 remains relatively large as schematically illustrated in FIG. 12 by section 45. A section 57 showing the cross-sectional area of the inlet 13 of the male enteral feeding connector 1 of FIG. 1 is juxtaposed with the section 45 in FIG. 12. As can be see, the cross-sectional area of the inlet 39, as illustrated by section 45, is significantly larger than the cross-sectional area of the inlet 13, illustrated by section 57. In one embodiment, the cross-sectional area of the augmented area section 45 is about 12.1 mm$^2$ (0.02 in.$^2$) and the cross-sectional area of section 57 is about 6.6 mm$^2$ (0.01 in.$^2$). In one embodiment, the cross-sectional area of the augmented area section 43 is over 180% larger than the cross-sectional area of section 57. Thus, the increased cross-sectional area for the inlet 39 of the assembly 21 allows passage of liquid that is thick and may include bits of solid, such as from ground fruit. The greater area also permits a greater flow rate to be generated into the enteral feeding connector 29 than can be generated with the cross-sectional area of the inlet 13 of the prior art, particularly under gravity feed. In the illustrated embodiment, there are two connector projections 61 disposed on opposite sides of the male connector portion 31 of the enteral feeding connector 29. It is envisioned, however, that any number of connector projections can be utilized. Other components for producing the opening diameter 63 in conformity of ISO standards 80369-3 (proposed) and 80369-20 are envisioned. For instance, cross ribs, bridges, and other projections disposed at different angles could be used to accomplish the increased flow rate and occlusion reduction while still conforming to the ISO standards.

In use, the enteral feeding syringe assembly 21 places the syringe 25 in fluid communication with the feeding tube 23 to deliver fluid through the feeding tube. The augmented area section 43 at the outlet 37 of the syringe 25, the augmented area section 45 at the inlet 39 of the enteral feeding connector 29, and the increased diameter of the flow passage 41 in the male connector portion 31 create increased cross-sectional areas which provide less constriction allow for a greater flow rate to be generated in these areas of the enteral feeding syringe assembly 21 than can be achieved with the syringe assembly shown in FIG. 1. Accordingly, the assembly 21 of the present invention is capable of accommodating thicker enteral feeding fluids that may include bits of solid food.

Figure 13A:
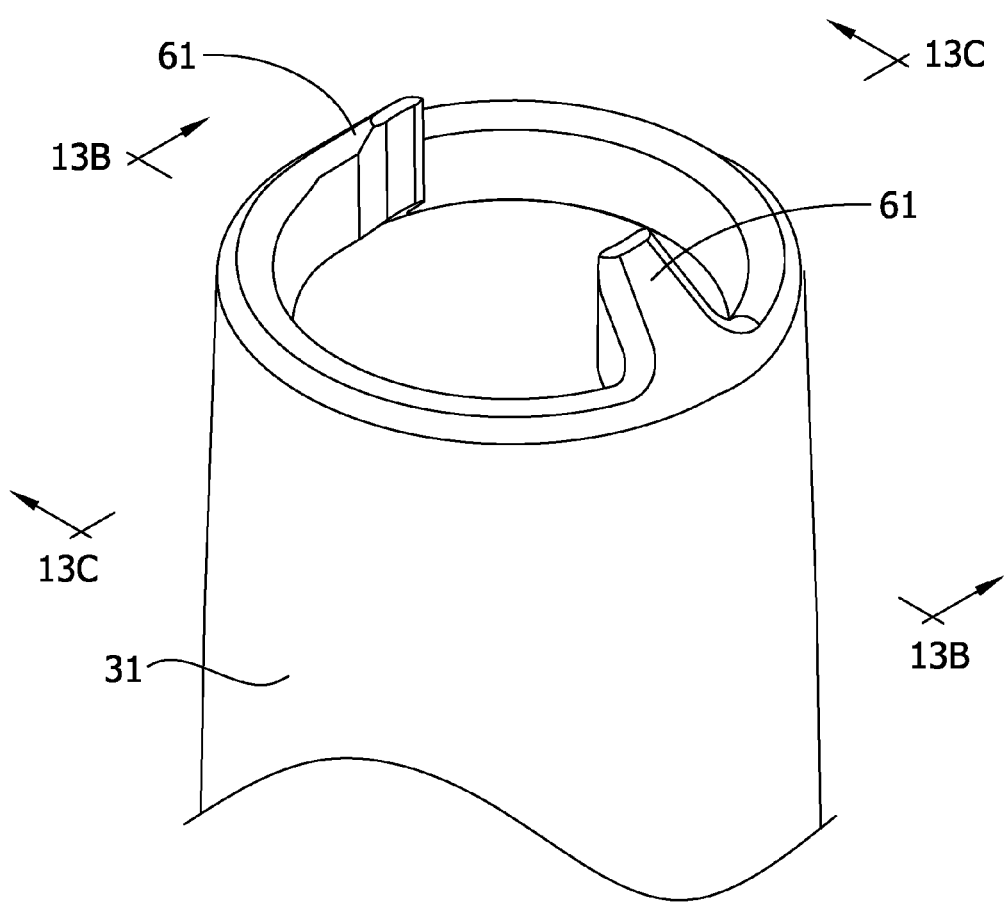
FIG. 13A is a fragmentary perspective of the male connector portion of the connector of the enteral feeding syringe assembly.
Figure 13B:
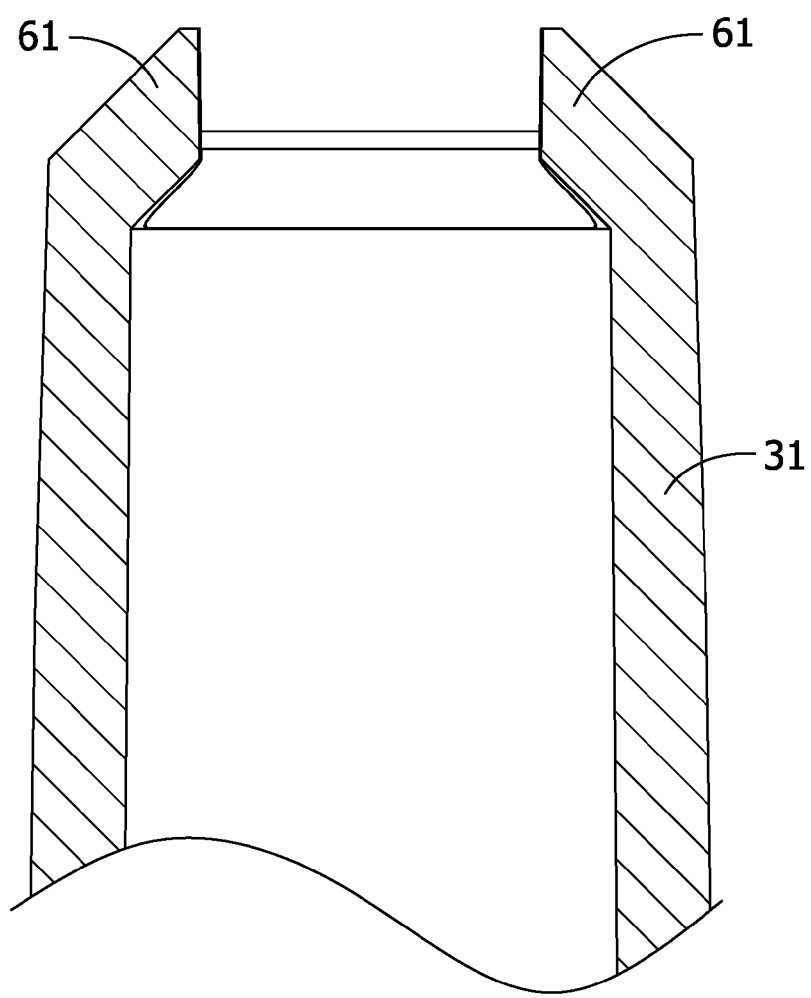
FIG. 13B is section of the male connector portion of FIG. 13A taken through line 13B-13B.
Figure 13C:
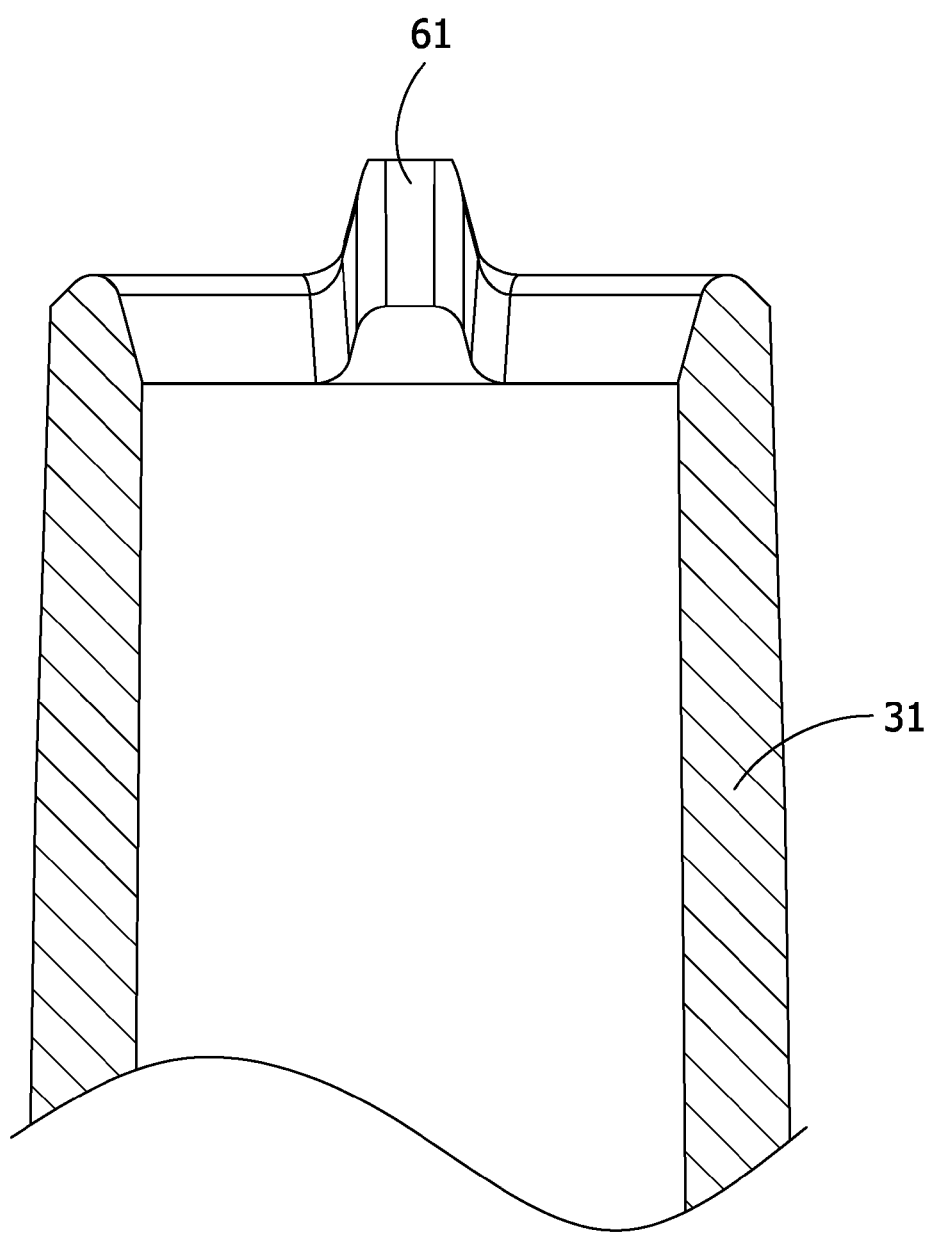
FIG. 13C is section of the male connector portion of FIG. 13A taken through line 13C-13C.
Figure 14A:
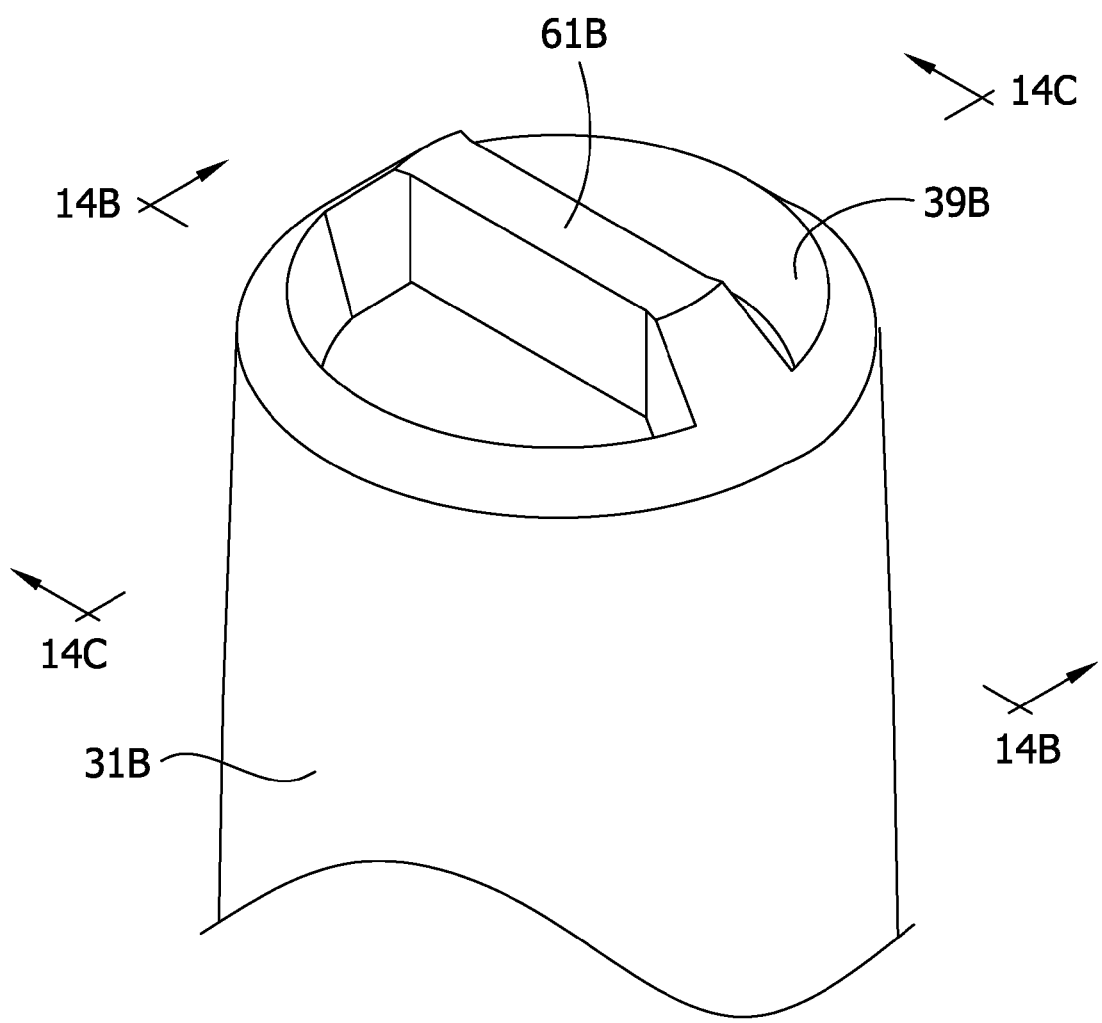
FIG. 14A is a fragmentary perspective of another embodiment of a male connector portion of the connector of the enteral feeding syringe assembly.
Figure 14B:
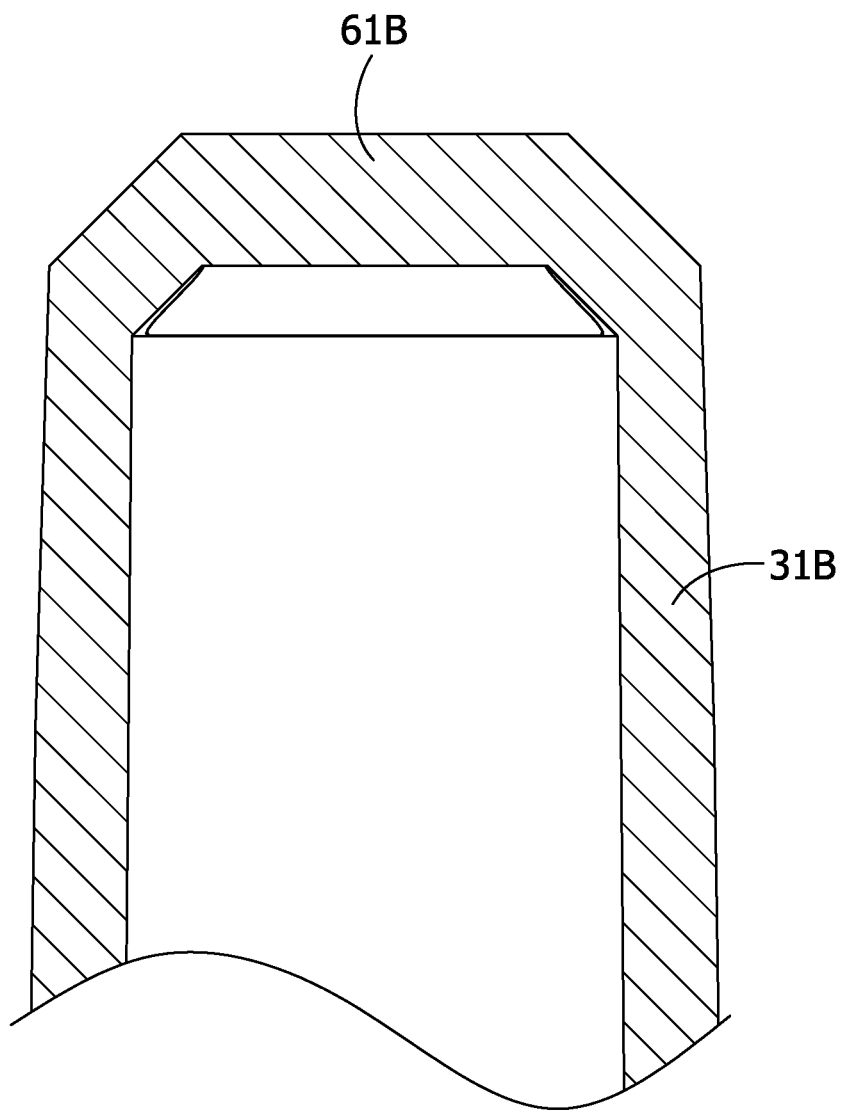
FIG. 14B is section of the male connector portion of FIG. 14A taken through line 14B-14B.
Figure 14C:
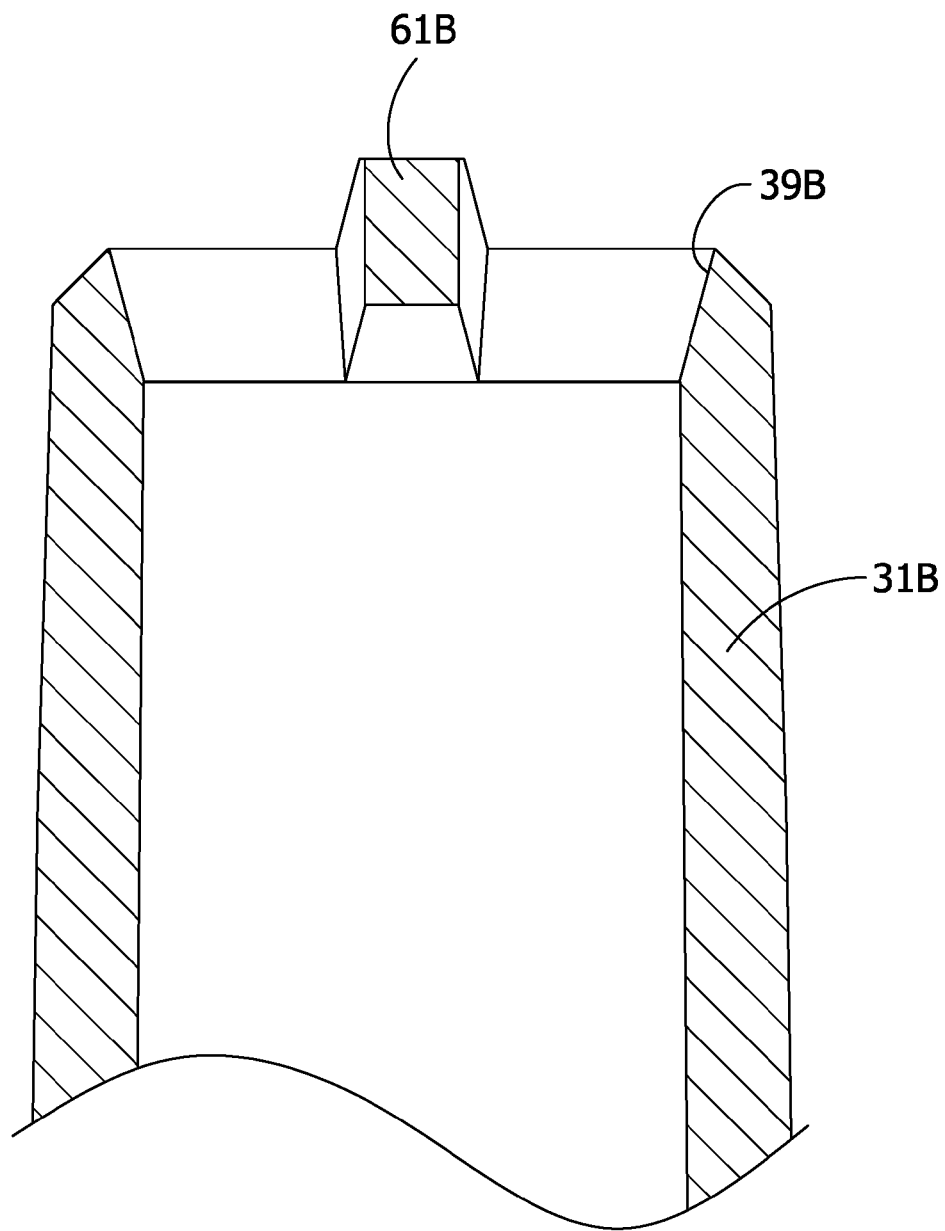
FIG. 14C is section of the male connector portion of FIG. 14A taken through line 14C-14C.
Figure 15A:
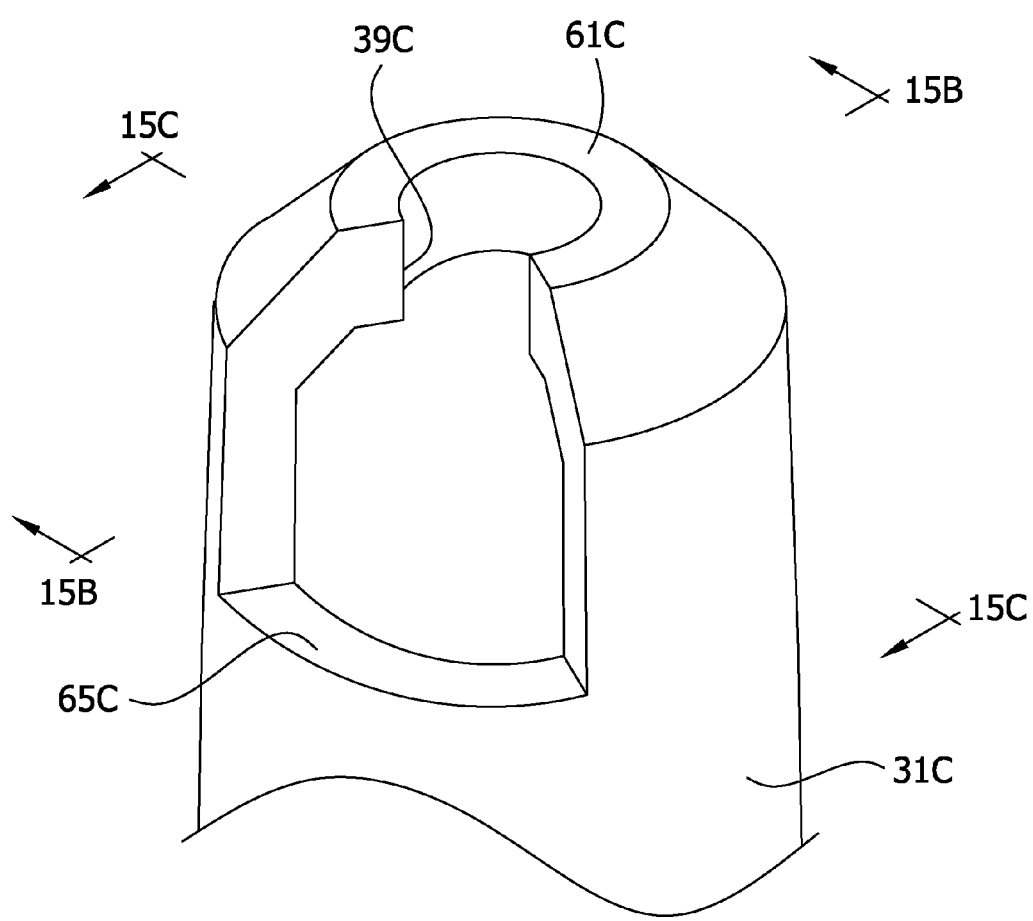
FIG. 15A is a fragmentary perspective of another embodiment of a male connector portion of the connector of the enteral feeding syringe assembly.
Figure 15B:
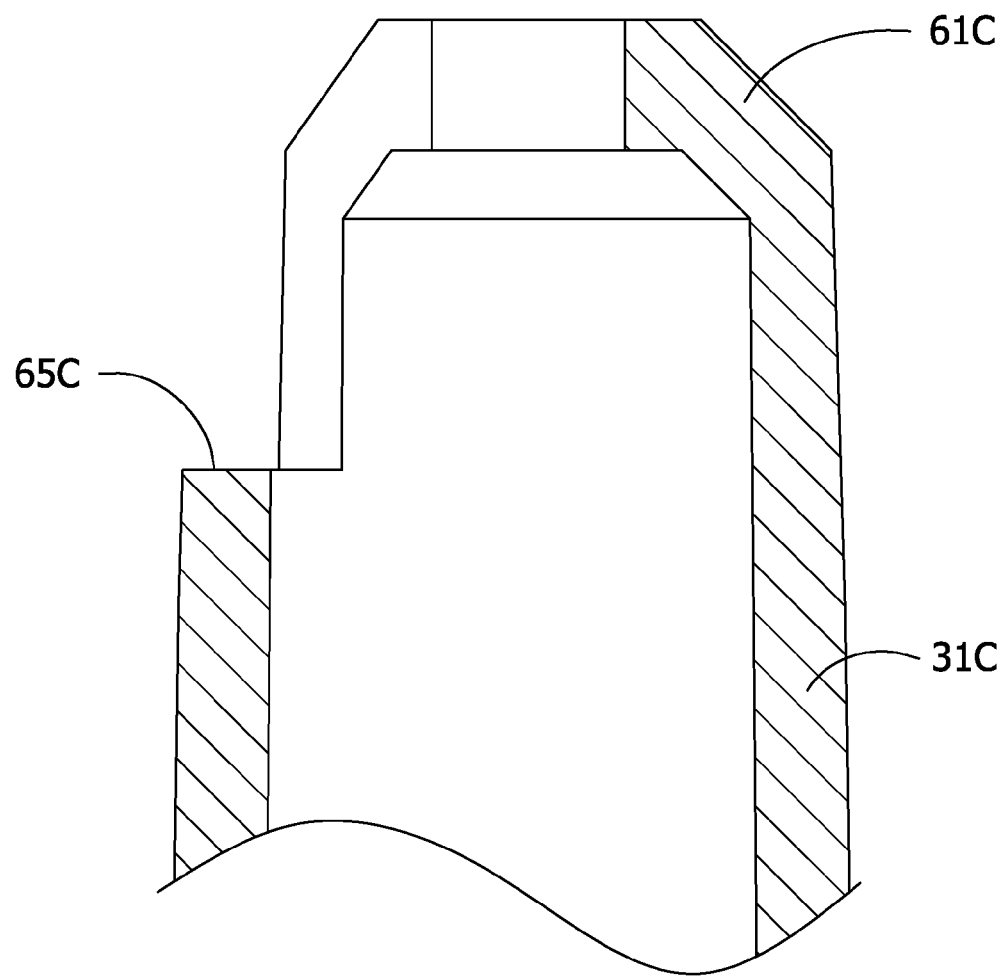
FIG. 15B is section of the male connector portion of FIG. 15A taken through line 15B-15B.
Figure 15C:
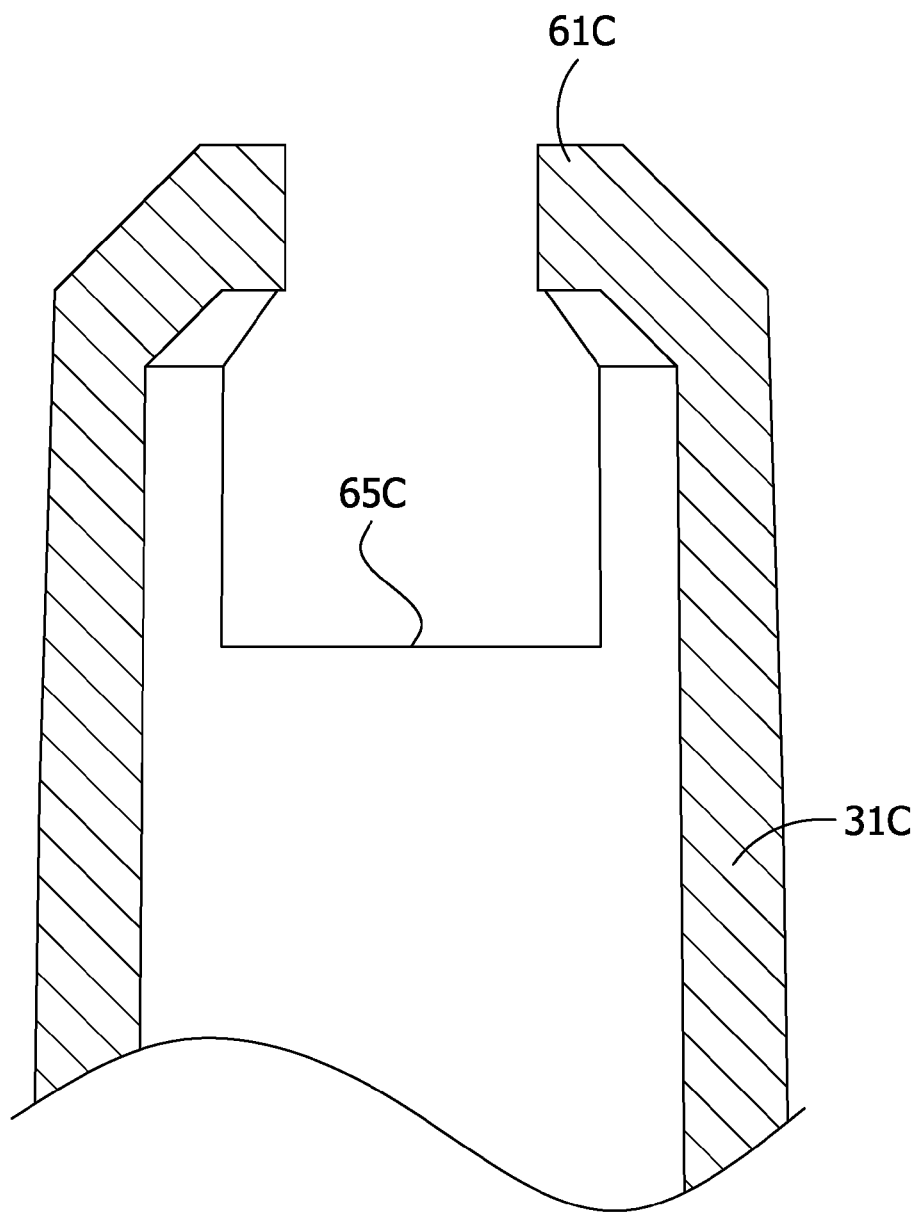
FIG. 15C is section of the male connector portion of FIG. 15A taken through line 15C-15C.

Referring to FIGS. 13A-17C, some alternative configurations for the male connector portion 31 are disclosed. FIGS. 13A-13C show male connector portion 31 and connector projection 61 described above. FIGS. 14A-14C illustrate a connector projection 61B extending across inlet 39B of male connector portion 31B. The areas to the sides of the connector projection 61B produce an augmented area portion of the inlet 39B. A distal portion of the connector projection 61B maintains the proposed 80369-3 ISO standard to prevent misconnection of the male connector portion 31B. FIGS. 15A-15C show a connector projection 61C that extends partially around inlet 39C of male connector portion 31C. A recess 65C is formed in the male connector portion 31C and extends around a remainder of the inlet 39C and down a side of the male connector portion. The recess 65C produces an augmented area portion at the inlet 39C. A distal portion of the connector projection 61C maintains the proposed 80369-3 ISO standard to prevent misconnection of the male connector portion 31C.

Figure 16A:
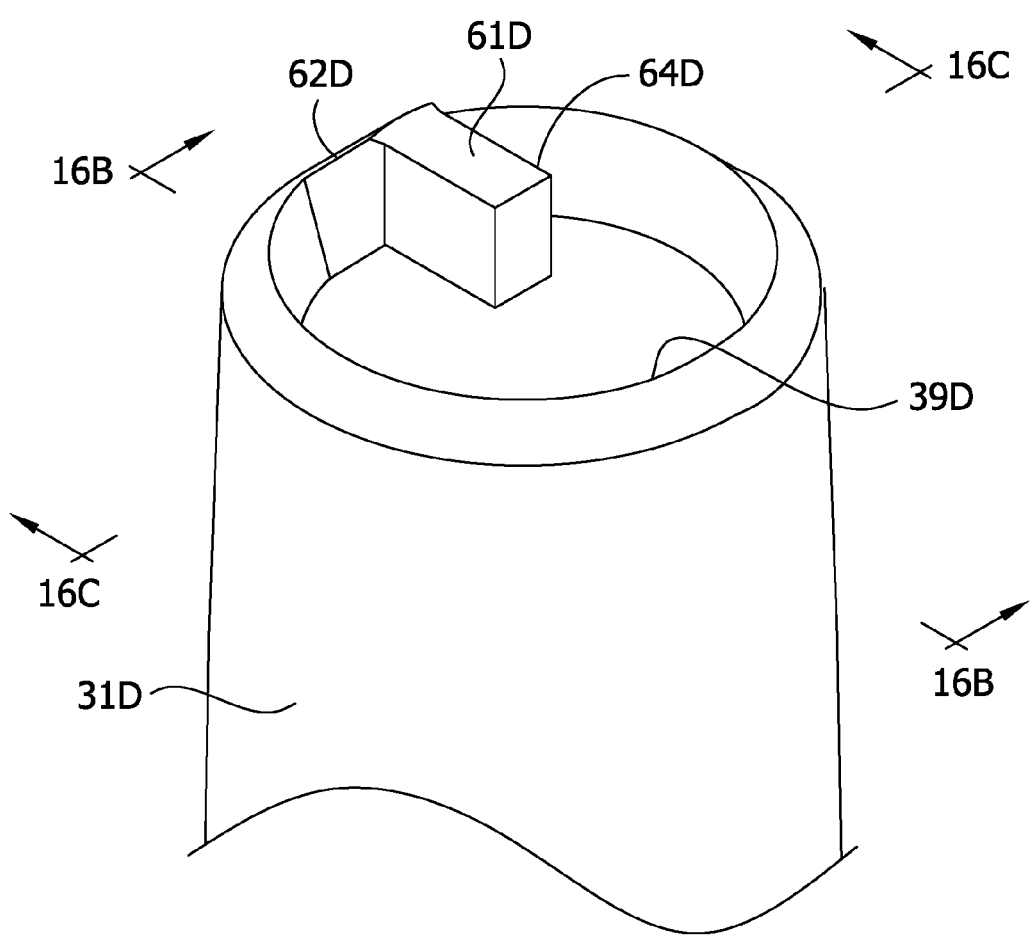
FIG. 16A is a fragmentary perspective of another embodiment of a male connector portion of the connector of the enteral feeding syringe assembly.
Figure 16B:
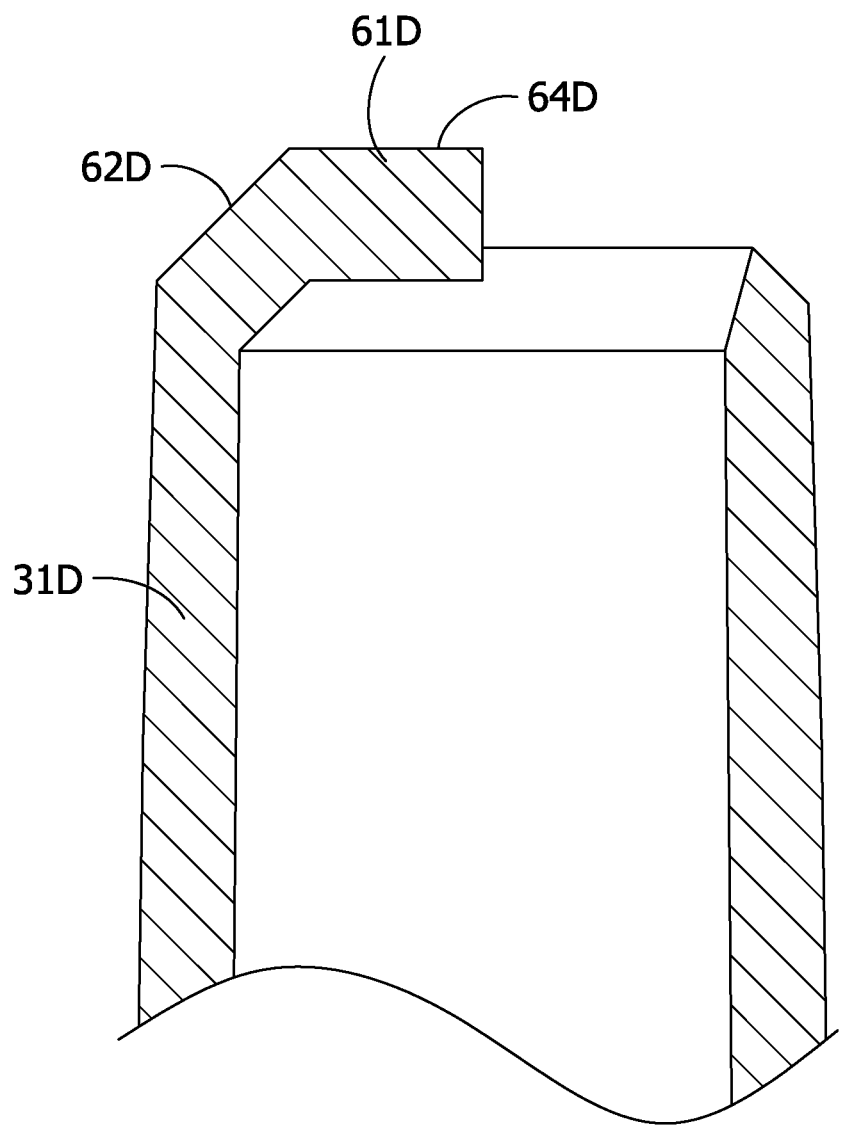
FIG. 16B is section of the male connector portion of FIG. 16A taken through line 16B-16B.
Figure 16C:
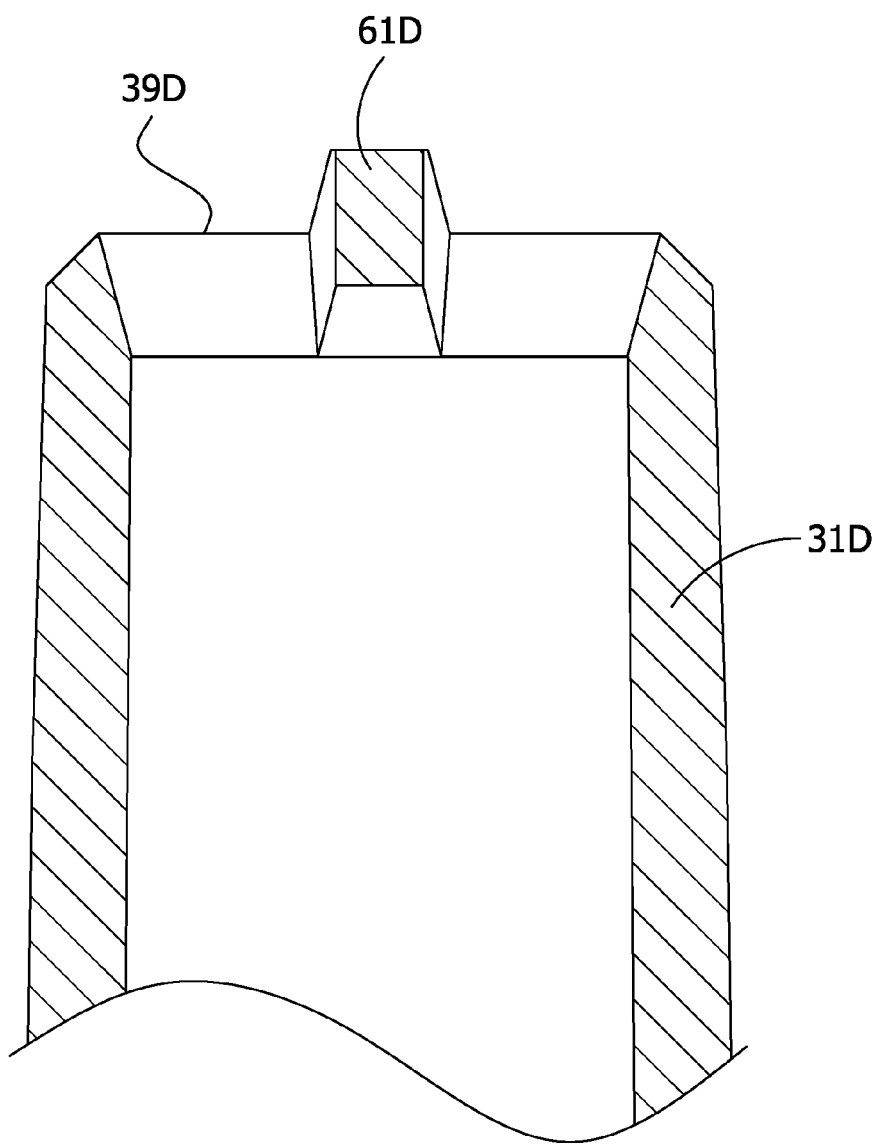
FIG. 16C is section of the male connector portion of FIG. 16A taken through line 16C-16C.
Figure 17A:
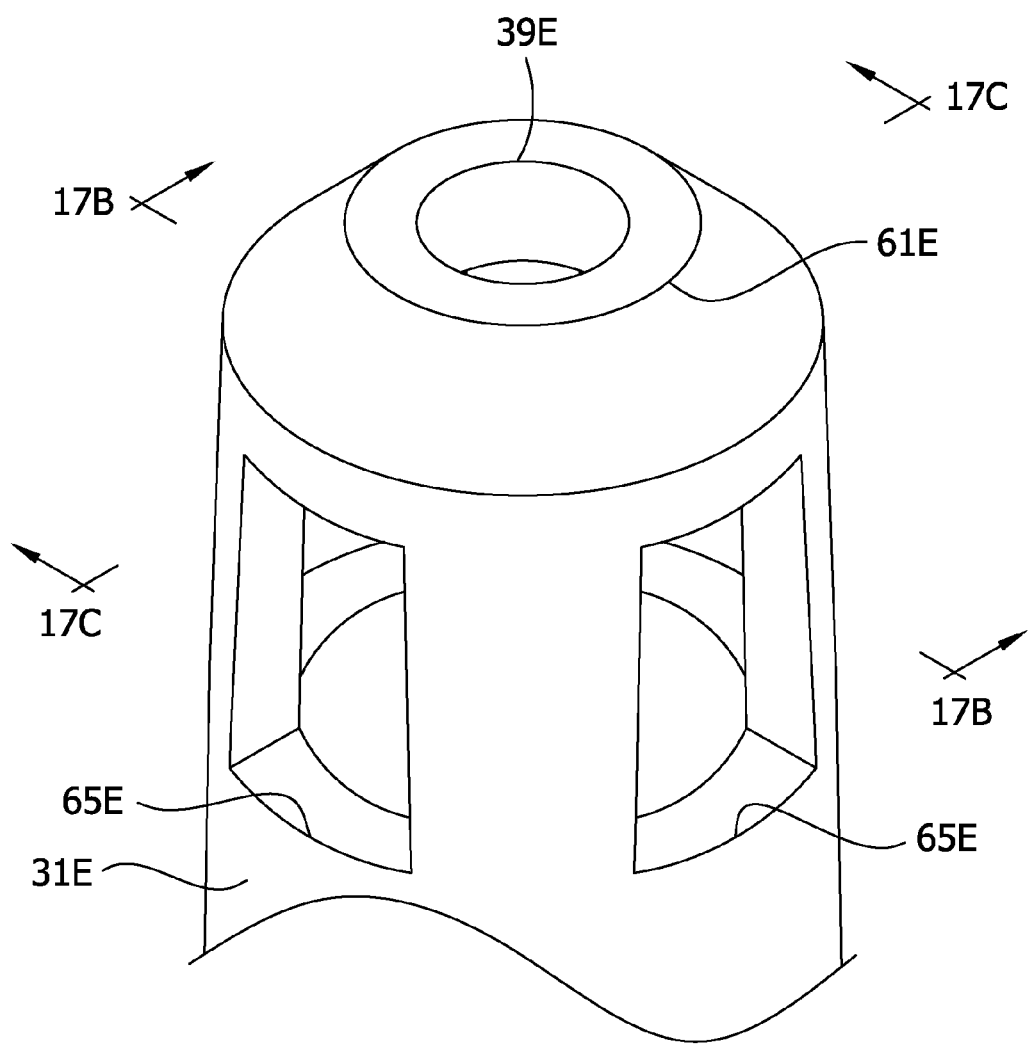
FIG. 17A is a fragmentary perspective of another embodiment of a male connector portion of the connector of the enteral feeding syringe assembly.
Figure 17B:
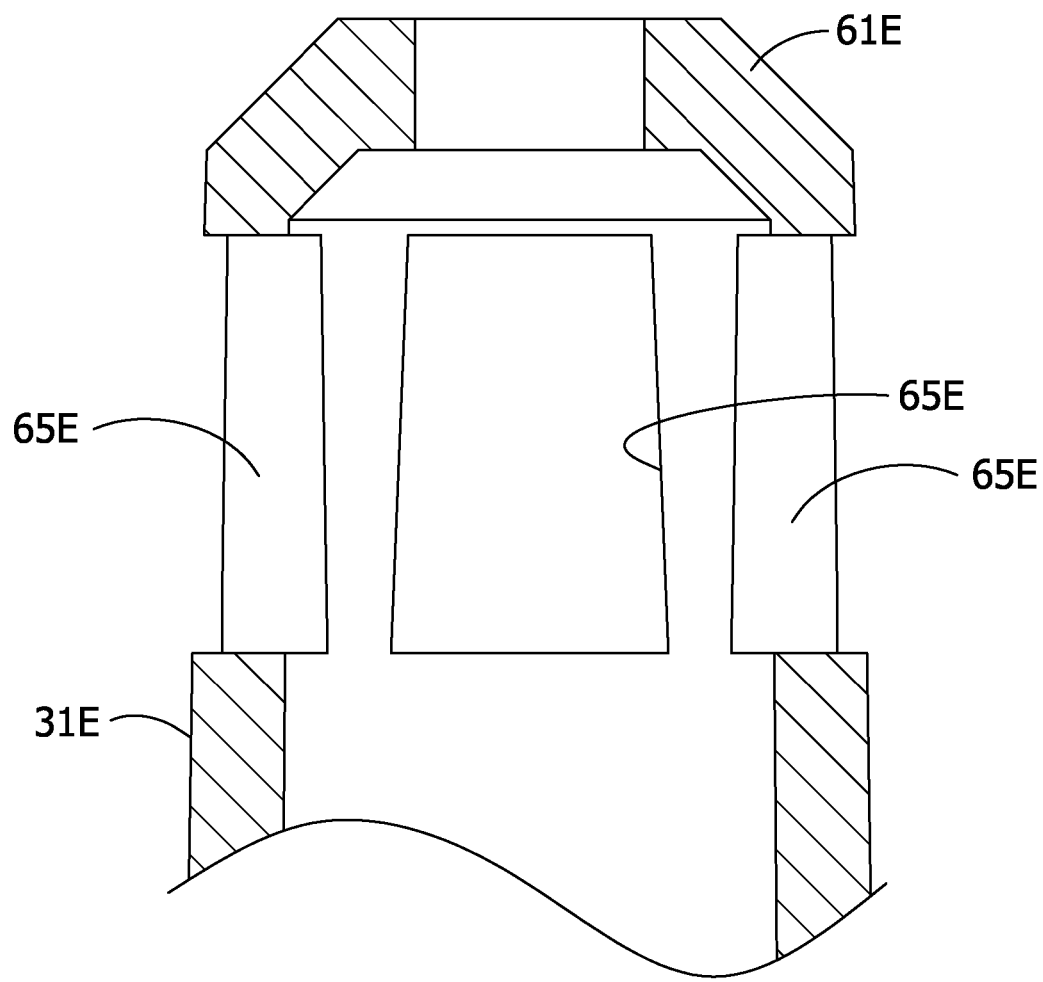
FIG. 17B is section of the male connector portion of FIG. 17A taken through line 17B-17B.
Figure 17C:
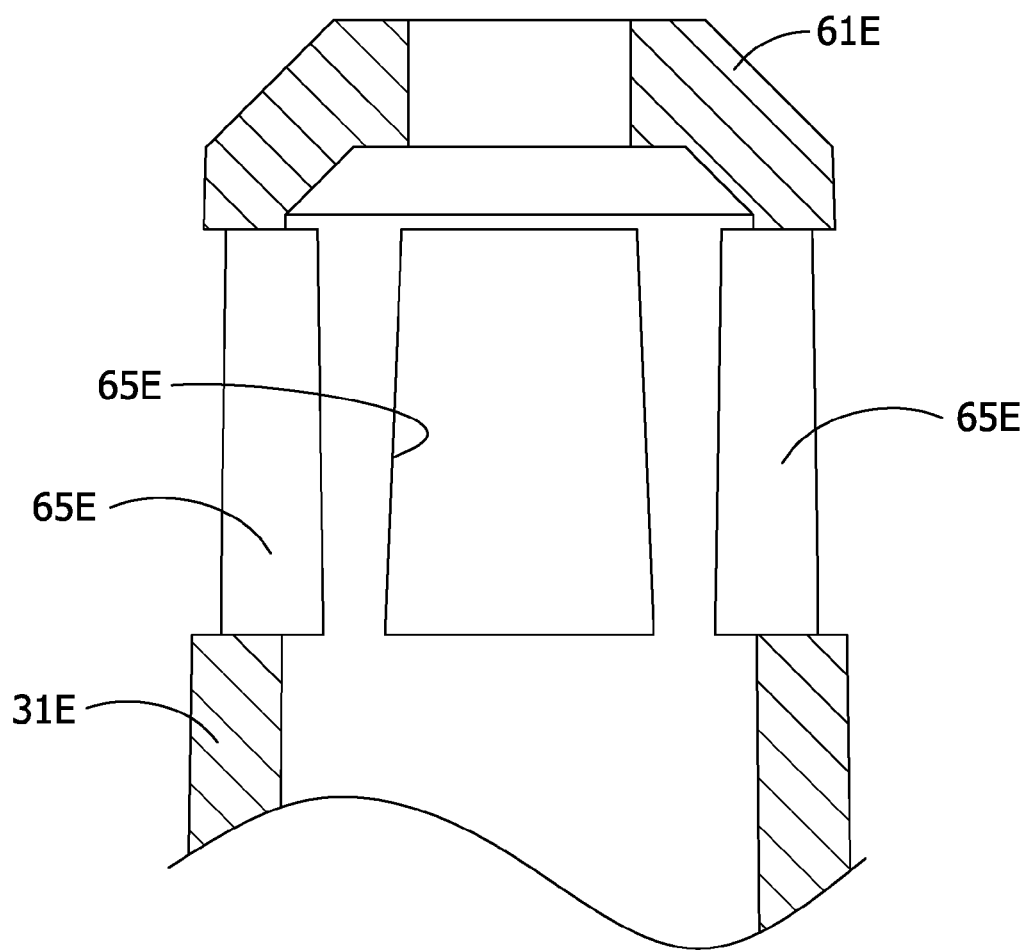
FIG. 17C is section of the male connector portion of FIG. 17A taken through line 17C-17C.

A male connector portion 31D having a single connector projection 61D extending partially across inlet 39D of male connector portion, is shown in FIGS. 16A-16C. The area around of the connector projection 61D is an augmented area portion at the inlet 39D. The connector projection 61D includes a first portion 62D extending away from the connector portion 31D and toward a longitudinal axis of the connector portion, and a second portion 64D extending laterally across the inlet 39D generally perpendicular to a longitudinal axis of the connector portion 31D. A distal portion of the connector projection 61D maintains the proposed 80369-3 ISO standard to prevent misconnection of the male connector portion 31D. For example, a distance between the free end of the projection 61D and the opposed edge of the inlet 39E may be less than 2.9 mm. FIGS. 17A-17C disclose cutouts 65E in male connector portion 31E. The cutouts 65E are disposed adjacent an inlet 39E of the male connector portion 31E. The cutouts 65E produce an augmented area portion allowing for a greater flow rate to be generated near the inlet 39E. In the embodiment of FIGS. 17A-17C, the male connector portion 31E seals with a female connector (e.g., female connector 27) at a location below the bottoms of the cutouts 65E. Thus, liquid may flow around the free end of the male connector portion 31E and into the cutouts 65E. A distal portion of the male connector portion 31E maintains the proposed 80369-3 ISO standard to prevent misconnection of the male connector portion. In the illustrated embodiment, the cutouts 65E have a trapezoidal shape. However, the cutouts 65E can have other shapes without departing from the scope of the disclosure.

Having described embodiments of the invention in detail, it will be apparent that modifications and variations are possible without departing from the scope of the invention defined in the appended claims.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An enteral feeding syringe assembly comprising:
a syringe including a barrel and a connector portion having a syringe fluid passage in fluid communication with the barrel and extending through the connector portion to a port of the syringe, the syringe fluid passage including a main portion defining a centerline of the syringe fluid passage and a constricted portion, the constricted portion including a first axially facing blocking surface of the connector portion defining at least a portion of a boundary of the constricted portion of the syringe fluid passage, a second axially facing surface located on a diametrically opposite side of the centerline from the first axially facing surface and defining at least a portion of the boundary of the constricted portion, and a third axially facing surface angularly offset about the centerline from the first axially facing surface and defining at least a portion of the boundary of the constricted portion, the third axially facing surface being spaced from the centerline a distance greater than at least one of the first and second axially facing surfaces; and
a connector configured for attachment to the syringe to connect the syringe in fluid communication with a fluid containment device, the connector comprising a male connector portion receivable in the fluid passage of the syringe connector portion, the male connector having a connector fluid passage extending through the connector, the connector fluid passage including a main portion defining a centerline of the connector fluid passage and a constricted portion, the constricted portion including a first axially facing blocking surface of the connector portion defining at least a portion of a boundary of the constricted portion of the connector fluid passage, a second axially facing surface located on a diametrically opposite side of the centerline from the first axially facing surface and defining at least a portion of the boundary of the constricted portion, and a third axially facing surface angularly offset about the centerline from the first axially facing surface and defining at least a portion of the boundary of the constricted portion, the third axially facing surface being spaced from the centerline a distance greater than at least one of the first and second axially facing surfaces.

2. The assembly of claim 1 wherein the connector portion of the syringe further comprises a connector projection of the connector portion extending toward the centerline of the syringe fluid passage, the first axial surface being defined on the connector projection.

3. The assembly of claim 2, wherein the connector projection of the syringe extends laterally across the syringe fluid passage of the connector portion of the syringe.

4. The assembly of claim 3, wherein the connector projection of the syringe comprises a first connector projection of the syringe, the syringe further comprising a second connector projection disposed on an opposite side of the centerline, the second connector projection extending laterally across the syringe fluid passage of the connector portion of the syringe, the second axially facing surface being defined on the second connector projection.

5. The assembly of claim 1, wherein the distance between the first and second axially facing surfaces is about 2.90 mm (0.11 in.) or less.

6. The assembly of claim 1, wherein the male connector portion of the connector comprises a connector projection extending toward the centerline of the connector fluid passage, the first axial surface of the male connector portion being defined in the connector projection.

7. The assembly of claim 6 wherein the connector projection of the male connector portion of the connector extends laterally across the fluid passage of the connector, the connector projection of the male connector portion is configured to extend into the syringe fluid passage of the connector portion of the syringe and make a sealing connection with the connector portion of the syringe when the connector is attached to the syringe.

8. The assembly of claim 7, wherein the connector projection of the connector comprises a first connector projection of the connector, the connector comprising a second connector projection disposed on an opposite side of the fluid passage of the connector, the second connector projection of the connector extending laterally across the fluid passage of the connector, the second axially facing surface being defined on the second connector projection.

9. The assembly of claim 8, wherein a distance between the first and second axially facing surfaces of the male connector portion of the connector is about 2.90 mm (0.11 in.) or less.

10. The assembly of claim 6, wherein the connector projection of the connector extends laterally across the fluid passage of the connector from one side of the fluid passage to the diametrically opposite side of the fluid passage.

11. The assembly of claim 1, wherein the connector projection of the connector includes a first portion extending away from the male connector portion at an angle toward a central longitudinal axis of the male connector portion, and a second portion extending from the first portion generally perpendicular to the central longitudinal axis of the male connector portion.

12. The assembly of claim 1, wherein the male connector portion includes at least one cutout in the male connector portion, the cutout providing an augmented area portion enhancing fluid flow in the passage of the male connector portion.

* * * * *